(12) United States Patent
Xia et al.

(10) Patent No.: US 10,376,712 B2
(45) Date of Patent: Aug. 13, 2019

(54) REAL-TIME APPLICATOR POSITION MONITORING SYSTEM

(71) Applicant: UNIVERSITY OF IOWA RESEARCH FOUNDATION, Iowa City, IA (US)

(72) Inventors: Junyi Xia, Iowa City, IA (US); Yusung Kim, Iowa City, IA (US); Timothy J. Waldron, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 109 days.

(21) Appl. No.: 15/366,537

(22) Filed: Dec. 1, 2016

(65) Prior Publication Data
US 2017/0239491 A1 Aug. 24, 2017

Related U.S. Application Data

(60) Provisional application No. 62/261,607, filed on Dec. 1, 2015.

(51) Int. Cl.
| | |
|---|---|
| *A61N 5/10* | (2006.01) |
| *A61B 34/20* | (2016.01) |
| *A61B 5/055* | (2006.01) |
| *A61B 5/00* | (2006.01) |
| *A61B 5/06* | (2006.01) |
| *A61B 90/00* | (2016.01) |

(52) U.S. Cl.
CPC ............ *A61N 5/1007* (2013.01); *A61B 5/004* (2013.01); *A61B 5/055* (2013.01); *A61B 5/064* (2013.01); *A61B 5/066* (2013.01); *A61B 5/7207* (2013.01); *A61B 34/20* (2016.02); *A61B 5/6851* (2013.01); *A61B 5/6852* (2013.01); *A61B 5/7257* (2013.01); *A61B 2034/2057* (2016.02); *A61B 2034/2065* (2016.02); *A61B 2090/397* (2016.02); *A61B 2090/3954* (2016.02); *A61B 2090/3966* (2016.02); *A61B 2090/3983* (2016.02); *A61B 2090/3995* (2016.02); *A61B 2560/0223* (2013.01); *A61N 2005/1055* (2013.01); *A61N 2005/1059* (2013.01); *A61N 2005/1061* (2013.01)

(58) Field of Classification Search
CPC .................. A61N 5/1001–1029; A61N 2005/1003–1025; A61N 2/00–12; A61B 5/06–068; A61B 34/20; A61B 2034/2046–2074
See application file for complete search history.

(56) References Cited

U.S. PATENT DOCUMENTS

| | | | | |
|---|---|---|---|---|
| 6,006,126 A | * | 12/1999 | Cosman | A61B 34/20 600/414 |
| 6,546,279 B1 | * | 4/2003 | Bova | A61B 8/0833 600/410 |
| 2017/0258531 A1 | * | 9/2017 | Bodjanski | A61B 34/20 |

* cited by examiner

Primary Examiner — Catherine B Kuhlman
(74) Attorney, Agent, or Firm — Smith Gambrell & Russell LLP

(57) ABSTRACT

A real-time applicator position monitoring system (RAPS) measures brachytherapy applicator displacement in real-time by computing the relative displacement between two infrared reflective targets, one attached to the applicator and the other to the patient's skin. In an aspect, RAPS can be used with any brachytherapy application. RAPS measures the applicator motion during HDR brachytherapy treatment, as well as during the transfer of the patient from the imaging room (e.g., where the CT and MR scanners are located) to the HDR BT operating/treatment room.

9 Claims, 19 Drawing Sheets

REAL-TIME APPLICATOR POSITION MONITORING SYSTEM

CLAIM OF PRIORITY

The present application claims priority from Provisional Patent Application No. 62/261,607, filed on Dec. 1, 2015, the disclosure of which is relied upon and incorporated herein in its entirety by reference.

FIELD OF THE INVENTION

The present invention relates to a positioning monitoring system utilized for brachytherapy.

BACKGROUND OF THE INVENTION

High Dose Rate (HDR) Brachytherapy (BT) is a form of radiation treatment in which a sealed radioactive source is introduced into the anatomy of a patient to be treated through an applicator. Recent advances in 3D image-based treatment planning for intracavity cancer BT, including, but not limited to, cervical cancer BT, have improved clinical outcomes. Effectiveness and accuracy of the treatment depends upon a fixed applicator position. Unless computerized tomography (CT) or magnetic resonance (MR) scanners are installed in the treatment room in which HDR BT is occurring, a patient must be transferred out of treatment room in order to perform 3D image guidance.

Even though 3D image guidance has improved clinical outcomes in BT applications, there are still some shortcomings. One of the challenges still faced when using 3D image guidance is when the applicator is displaced from the specific placement on or within the body of the patient. Applicator displacement frequently occurs when patients are transferred between the treatment room and the imaging room in instances wherein CT or MR scanners are not found in HDR BT operating rooms. In addition, displacements occur between applicator insertions, during patient relocations, and during prolonged periods between imaging and treatment. Further, in gynecologic interstitial BT, needles or catheter displacements were caused by patient movement, or needles inadequately secured to the template.

3D imaging based, conformal BT has a tight target (e.g. high risk CTV) coverage with high dose-gradient. Therefore, a small applicator displacement can cause a significant radiation dose changes between intended doses and delivered doses. These displacements resulted in shifts of source dwell position relative to the target structures and organs at risk (OAR), altering the delivered dose. For example, De Leeuw et al. reported an average displacement of 3-4 mm in the cranial-caudal direction resulting in an average dose change of 4% to the rectum. Gerszten et al. reported up to 12 mm displacement, when using an applicator-immobilization device. Kim et al. reported up to 2.4 mm displacement when using an in-house developed applicator-immobilization system.

Given the potential displacement, there is a need to monitor the displacement. In some instances, to monitor the potential applicator displacement, an X-ray is taken before and after a patient transfer to 3D image (CT or MRJ) scan. However, 2D X-ray is limited to show applicator displacement. In addition, no real-time monitoring is possible, since fluoroscopy imaging would require such a significant radiation dose to which a patient cannot be used to do real-time monitoring for an applicator. It has been reported 3 mm displacement of applicator causes 10% dosimetric error in HDR or Pulse-Dose-Rate BT. Therefore it is desirable to have some means to ensure no motion of the applicator occurs.

Several techniques and products have been used to address applicator or needle displacement. The Zephyr system (DIACOR Inc., Salt Lake City, Utah) uses an air-bearing technique whereas the MedTrack system (MedTrack, LLC, Madison, Wis.) uses ceiling rails. Needles can be secured with a variety of techniques, including buttons or adhesive. However, fixation techniques do not address applicator and needle immobilization. If an immobilization device is rigidly attached to a transfer-table, incidental patient motion can harm the patient. Therefore immobilization devices should be attached to the patient to follow their movement. Even with an immobilization device, applicator displacement of up to 2.4 mm (10) and 12 mm (4) has been reported. The displacement can have an impact on the treatment. For example, the dosimetric impact of applicator shifts was reported to be an average change of 3-5% on rectum per mm of applicator displacement in cranial-caudal direction.

In gynecological HDR BT, applicator displacement can be measured using reference points and markers on the bony anatomy. Hoskin et al. investigated applicator displacement using the distance between the ovoid source and bladder or rectal reference points. Significant applicator displacement was observed in the cranial-caudal direction relative to ICRU bladder point. Small applicator displacement relative to ICRU bladder point (median: 2 mm, range: 0-10 mm) was observed in anterior-posterior direction. These displacements were attributed to placement techniques and vaginal packing. Similar studies measured applicator displacement using a set of markers placed on the bony anatomy and dummy marker reference points inserted into the applicator. Bahena et al. investigated applicator displacement of the ring and tandem applicator relative to the bony anatomy. Using anterior-posterior and lateral orthogonal images, the applicator position was established using 4 bony landmarks of the pelvis and dummy marker reference points on the applicator. The reproducibility of the applicator position was measured by comparing the applicator positions in the subsequent implant to the position in the first implant. A displacement of 6.5, 5.9 and 7.7 mm was observed in the superior-inferior direction, lateral direction and anterior posterior direction respectively, which was due to changes of both tumor volume and anatomy during the course of treatment.

Pham et al. evaluated the change in the applicator position during multiple HDR insertions using an unfixed tandem and ovoid applicator system. The changes in the applicator position were measured relative to the patient's bony pelvic landmarks. The authors observed an average longitudinal displacement of 3 mm for the tandem and 2 mm for the Ovoids. Thomadsen et al's. study used a fixed HDR applicator system and observed an average shift of 1.7 mm relative to the bony pelvis even though the applicators were fixed to the treatment table. Several studies have examined the displacement inherent in gynecologic interstitial BT. Mikami et al. measured the distance between the applicator tip and the reference point of center of gravity of the three implanted titanium markers. Significant applicator displacement was observed in the caudal direction (median: 1 mm, range: −6 to 12 mm). Shukla et al. noted a 17 mm applicator displacement in the caudal direction. Using a template like the Syed-Neblett system, Damato et al inserted dummy markers into the applicator to identify the tips on computed tomography (CT) scans. Two CT scans of the pubic symphysis were used for rigid registration of the applicator shift, where the authors observed needle displacement up to 20.0 mm in the cranial direction and 16.3 mm in the caudal direction.

Current applicator tracking techniques are not able to provide continuous and real time measurements while applicator displacement can also be caused by incidental patient motion after the 3D scan and during treatment delivery. Currently, no commercial system is available for continuous monitoring applicator motion. Those commercial solutions available only takes snapshots of applicator using either CT or C-arm based X-ray systems, so they cannot be used for continuous monitoring due to high imaging dose.

Therefore, there is a need for a system and method for providing continuous and real time measurements of applicator displacement. Further, there is such a need for such a system and method that does not require additional imaging that does not expose the patient to high imaging dosage.

SUMMARY OF THE INVENTION

The invention of the present application is directed to systems and methods of real-time monitoring of a brachytherapy (BT) applicator displacement. In an aspect, the invention comprises a real-time applicator position monitoring system (RAPS) that measures BT applicator displacement in real-time by computing the relative displacement between at least two infrared reflective targets, one attached to the applicator and the other to the patient's skin. In an aspect, the RAPS can be used with any BT application. The RAPS measures the applicator motion during HDR BT treatment, as well as during the transfer of the patient from the imaging room (e.g., where the CT and MR scanners are located) to the HDR BT operating/treatment room. The real-time HDR applicator position information that is provided by RAPS allows clinicians to make proper corrections when unacceptable applicator displacements occur.

In an aspect, the RAPS includes image processing and displacement software for controlled image acquisition, image processing, marker detection and computation of applicator displacements. By measuring the relative change in distance between the applicator marker and the patient marker, RAPS can monitor applicator displacements. This invention can be used in HDR BT where high applicator position accuracy is required.

These and other aspects of the invention can be realized from a reading and understanding of the detailed description and drawings.

BRIEF DESCRIPTION OF THE DRAWINGS

FIGS. 9(c-d) illustrate overlapped images of the reference image in inverted gray scale and the registered target image at non-displaced X-ray tube position and displaced X-ray tube position.

DETAILED DESCRIPTION OF THE INVENTION

Figure 1:
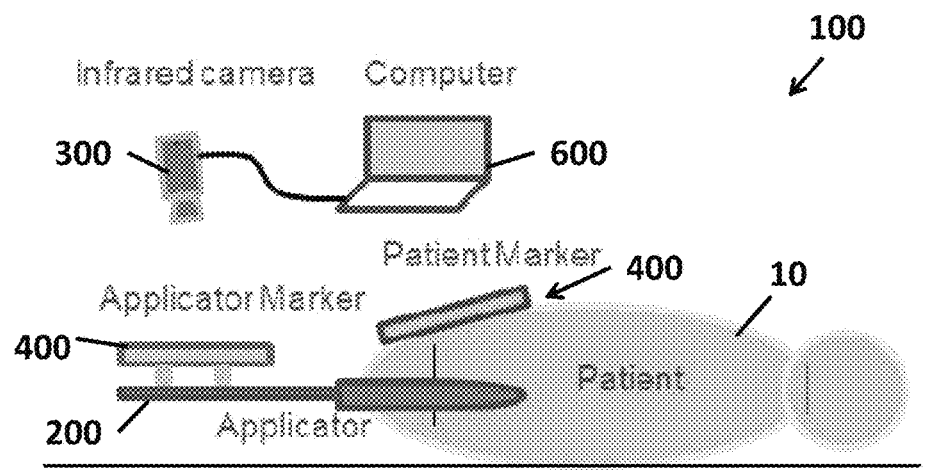
FIG. 1 is a schematic view of the PARS system according to an aspect of the present invention.

In an aspect, the real-time applicator position monitoring system ("RAPS") 100 is configured to measure displacement, in real-time, of a brachytherapy (BT) applicator 200 after intracavity insertion into the body 10 of a patient and through the applied treatment. In an aspect, the RAPS 100 comprises a BT applicator 200, a camera 300, markers 400, 500, and a computing device 600 having image processing and displacement software, as shown in FIGS. 1-3, 5, 7, and 7(a-b). The RAPS 100 is configured to continuously monitor the BT applicator 200 and its displacement within the body 10 of the patient during treatment. In an aspect, the RAPS 100 uses the camera 400 to capture images of the applicator 200 and the markers 400, 500, which are continuously sent to the computing device 600 to be processed by the image processing and displacement software 607 to display the applicator displacement (e.g., see FIG. 3). In an aspect, the RAPS 100 can capture a baseline measurement before or after any imaging once the applicator 200 has been inserted, and then can continuously monitor the applicator 200, through the use of the markers 400, 500, for displacement of the applicator 200 within the body 10.

In an aspect, the RAPS 100 is configured to be portable. In an aspect, some or all of the components of the RAPS 100 are of a size that allows them to be placed on movable carts 700 (see FIG. 2). The RAPS 100 can then be used from after the time of the insertion of the applicator 200 and during HDR BT, with the RAPS 100 traveling with the patient (i.e., the body 10) on a cart 700 from the imaging room to the HDR BT operating/treatment room. In an aspect, the cart 700 can include an uninterruptible power supply (UPS) unit (not shown), which can power the components of the RAPS 100 needing electricity. In an aspect, the applicator 200 can be any applicator 200 that can deliver HDR BT. In addition, the applicator 200, and the radiation source within the applicator, can be controlled by an HDR control unit (See FIG. 7).

In an aspect, the RAPS 100 uses at least one camera 300 to capture the location of the markers 400, 500 in relation to one another, the body 10 of the patient, and the applicator 200 within the patient. In an aspect, multiple cameras 300 can be used. In an aspect, the markers 400, 500 are configured to be coupled to the body 10 of the patient and the applicator 200, discussed in more detail below. In an aspect, the markers 400, 500 are configured to help the camera(s) 300 capture the positions of the applicator 200 and the body 10 of the patient relative to one another. In an aspect, the RAPS 200 can include patient markers 400 that are configured to be coupled to the body 10 of the patient and applicator markers 500 which are configured to be coupled to the applicator 200. In an aspect, the patient markers 400 and the applicator markers 500 have the same properties and characteristics discussed below.

In some aspects, the markers 400, 500 are configured to be reflective markers 400, 500 (see FIGS. 1-3, 5, 7, and 7(a-b)). In an exemplary aspect, the reflective markers 400, 500 are infrared reflective markers, reflecting infrared illumination to be captured by the camera(s) 300. In some instances, the infrared reflective markers 400, 500 are self-calibrated, especially when only one infrared camera 300 is used, as discussed below. However, in instances in which multiple infrared cameras 300 are employed, the infrared reflective markers 400, 500 do not need to be self-calibrating. In an aspect, a camera 300 can provide the illumination for the infrared reflective markers 400, 500, using an infrared illuminator 320 (see FIG. 2). In other aspects, the markers 400, 500 can provide their own illumination. In an aspect, the markers 400, 500 are configured to be reusable between different operations/patients. In such aspects, the markers 400, 500 are made of materials that can withstand multiple disinfectant procedures.

In an aspect, the markers 400, 500 can be computed tomography (CT) and magnetic resonance imaging (MM) compatible. In such instances, the markers 400, 500 are absent metal components, but are still made of durable materials. In an aspect, the reflective markers 400, 500 are made from ABS plastics. In addition, since the markers 400, 500 are configured to be placed on portions of patient's bodies 10 (i.e., 400), or on applicators 200 (i.e., 500) being placed within the bodies 10, it is preferable for the markers 400, 500 to be light-weight. By making the markers 400, 500 light weight, the discomfort of the patient is minimized, as well as minimizing the impact the weight of the marker(s) 500 will have on applicator displacement, especially with the applicator marker 500.

Since the markers 400, 500 are read by the camera(s) 300, the markers 400, 500 are configured to remain outside of the cavity of the body 10 of the patient. In an aspect, the RAPS 100 utilizes at least two markers 400, 500, one patient marker 400 that is configured to be placed or attached to the body 10 of the patient, and one applicator marker 500 configured to be coupled to the applicator 200. In another aspect, the RAPS 100 can utilize three markers 400: one marker 400 for the applicator 200 and two markers for body 10 of the patient, or vice versa. In other aspects, if multiple applicators 200 are being used, the RAPS 100 can include at least one marker 400 for each applicator 200 and at least one marker for the patient's body 10.

Figure 5:
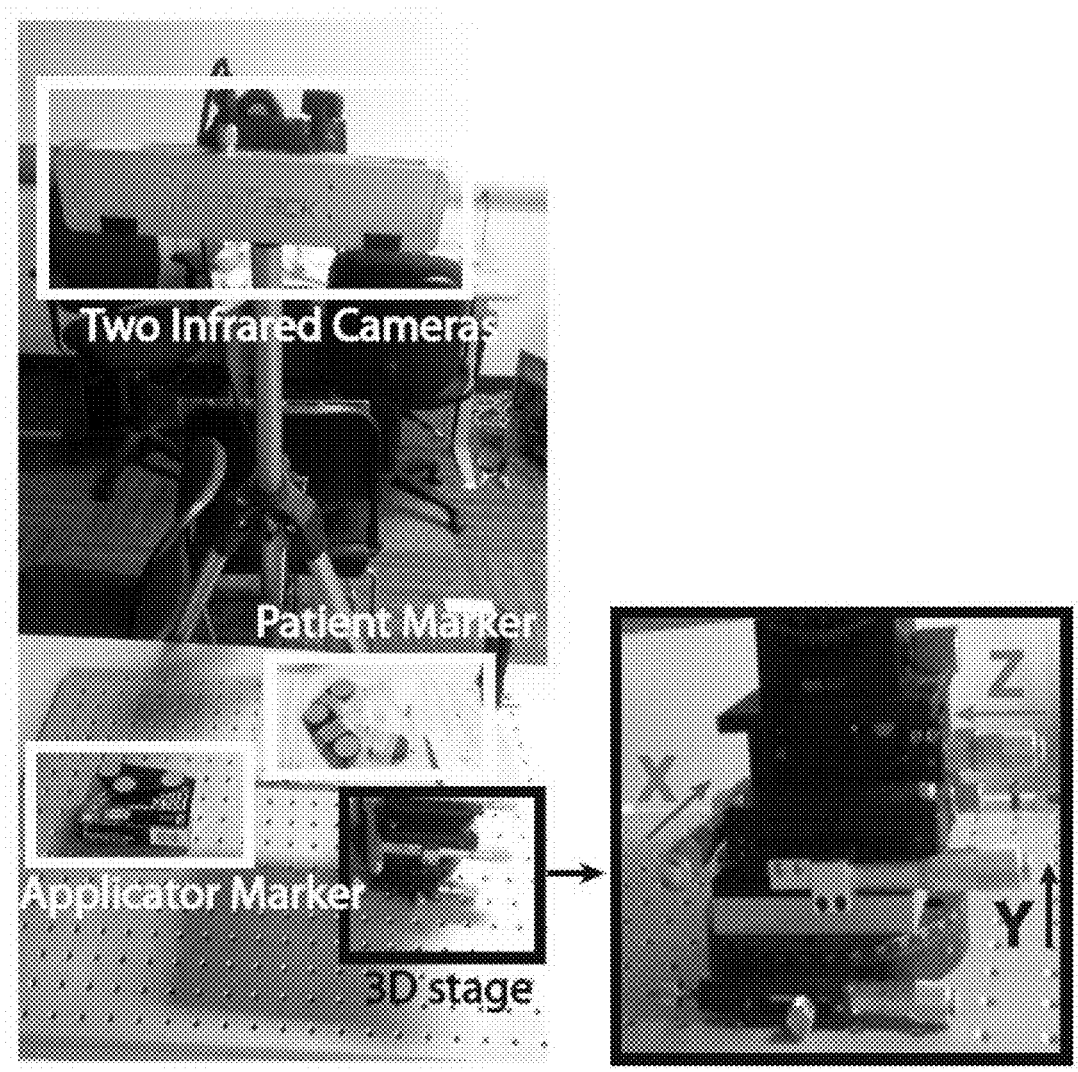
FIGS. 5 and 5(a)-5(c) show an experimental setup of RAPS's phantom study according to an aspect of the present invention.
Figure 5A:
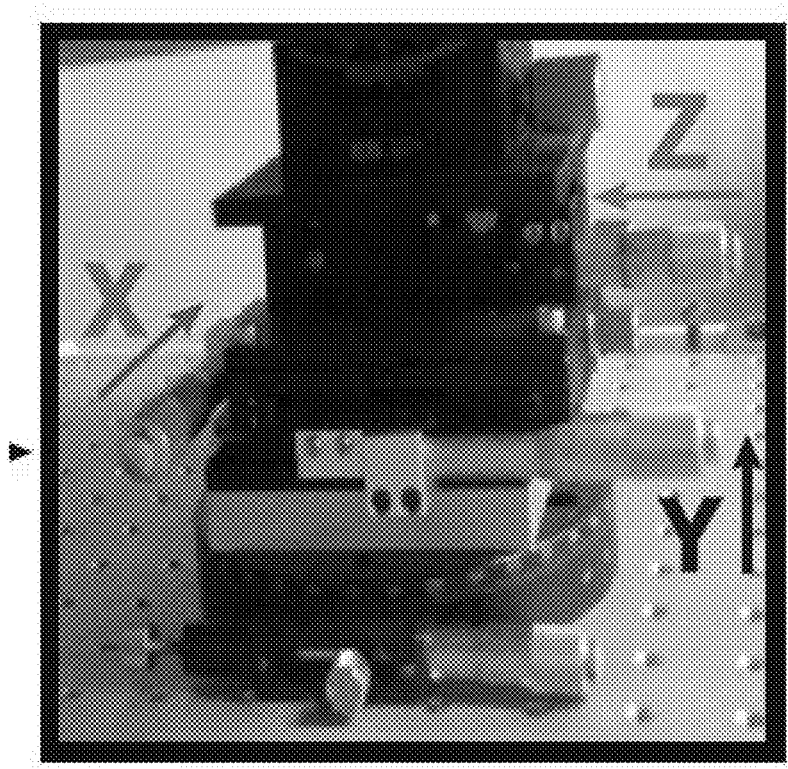
Figure 5B:
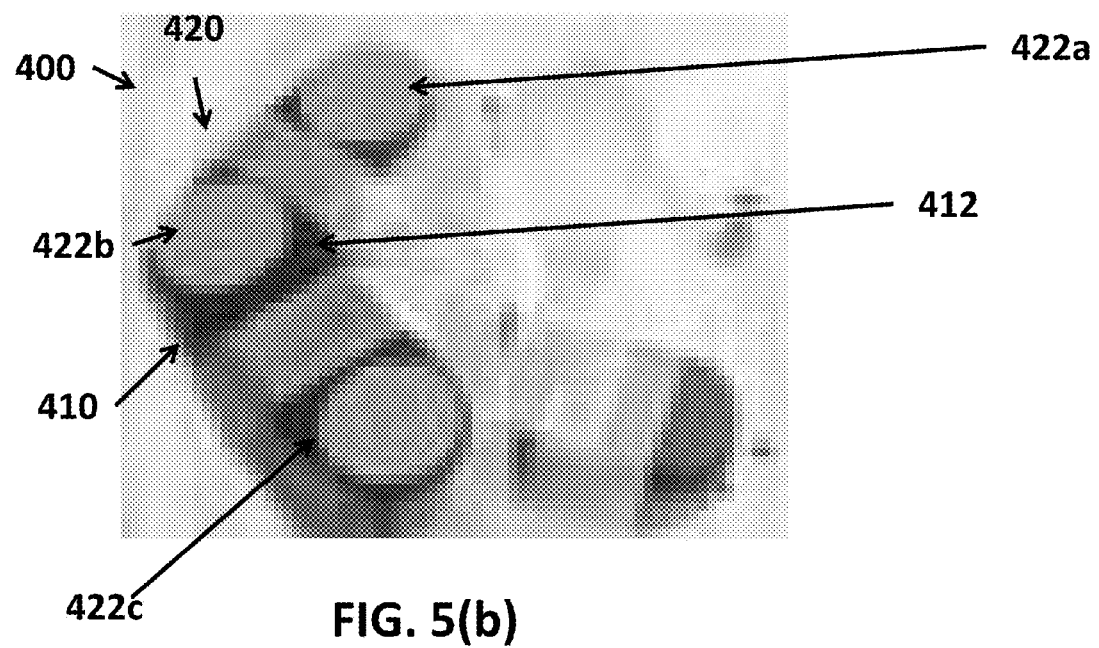
Figure 5C:
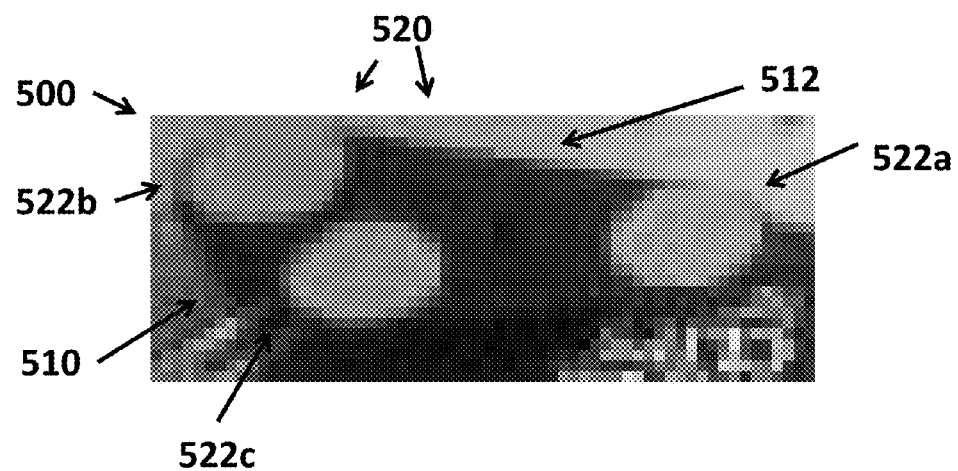

In an aspect, as shown in FIGS. 5, 5(a-b), and 7(a-b), the markers 400, 500 include a body 410, 510 with a top surface 412, 512 and a bottom surface (not shown). In an aspect, the body 410, 510 can also include a side surface as well. In an aspect, the top surface 412, 512 or the side surface is configured to have reflective means 420, 520. The reflective means 420, 520 can include indicators 422, 522 located at various portions along the top surface 412, 512. The indicators 422, 522 can be comprised of reflective tape or other reflective materials which can be mounted or embedded into the top surface 412, 512.

In an aspect, the markers 400, 500 include multiple reflective means 420, 520 on the upper surface 412, 512. As discussed above, these reflective means 420, 520 can include different surfaces and/or indicators 422, 522. These surfaces/indicators 422, 522 are configured to be tracked by the camera 300. The multiple reflective surfaces/indicators 422, 522 should be distinguishable from one another so the camera 300 can determine the orientation of the bodies 410, 510 of the markers 400, 500 as displacement occurs. In an aspect, the markers 400, 500 include at least two distinguishable reflective surfaces/means 422a/b, 522a/b. In a preferred aspect, each marker 400, 500 includes three distinguishable reflective surfaces/indicators 422a/b/c, 522a/b/c. While the distinguishable reflective surfaces/indicators 422a/b/c, 522/a/b/c can be arranged along the body 410, 510 of the markers 400, 500 in any configuration, it is preferable to have the distinguishable reflective surfaces/indicators/means 422, 522 be oriented on the same side of the body 410, 510 preferably the top surface 412, 512, opposite of the attachment means, in order to provide an unobstructed view for the camera 300. In some instances, the side surface can host the reflective means 422, 522.

The bottom surface (not shown) of the marker(s) 400, 500 can be configured to be coupled to attachment means. The attachment means are configured to couple the markers 400, 500 to the body 10 of the patient and the applicator 200 respectively. Various attachment means can be used to attach the markers 400, 500. In some cases, the attachment mean varies based on the intent of attachment. For example, the attachment means can include a fastener when being used to attach the marker 500 with an applicator 200. When the marker 400 is being attached to the patient, the attachment means can include various adhesives, including, but not limited to, double-sided tape, and skin-glue.

In an aspect, the bodies 410, 510 of the markers 400, 500 can come in various shapes and sizes. In some aspects, the type of HDR BT (i.e., where the treatment is targeted) can determine the shape and size of the bodies 410, 510. For example, in cervical cancer HDR BT, the patient marker 400 can have an L-shape body 410, while the applicator marker 500 can have a triangular shape body 510 (e.g., see FIGS. 5, 5(a-b), and 7(b)). However, other shapes can be utilized in cervical cancer HDR BT and other forms of HDR BT. In an aspect, the reflective means 420, 520 can determine the shape of the body 410, 510 of the markers 400, 500.

In addition to the markers 400, 500 the RAPS 100 includes a camera 300. The camera 300 is configured to capture the position of applicator 200 in relation to the body 10 of the patient, via the markers 400, 500, in real time. In an aspect, the camera 300 comprises an infrared camera 300. In an exemplarily aspect, the camera 300 comprises an infrared camera 300 and an infrared illuminator 320. In such aspects, the infrared illuminator 320 is configured to illuminate the reflective surfaces/indicators/means 420, 520 of the reflective markers 400, 500. However, in other embodiments, other types of cameras 300 can be used, including, but not limited to, depth cameras or regular color cameras. In such instances, the camera 300 and the markers 400, 500 must be able to work in concert with one another to track the displacement of the applicator 200 from the applicator's original location within body 10 of the patient. In an aspect, one camera 300 can be used. In an exemplary aspect, two cameras 300 are used (see FIGS. 5 and 7) in order to assist in capturing the displacement of the markers 400 in three dimensions, ensuring greater accuracy.

Figure 8:
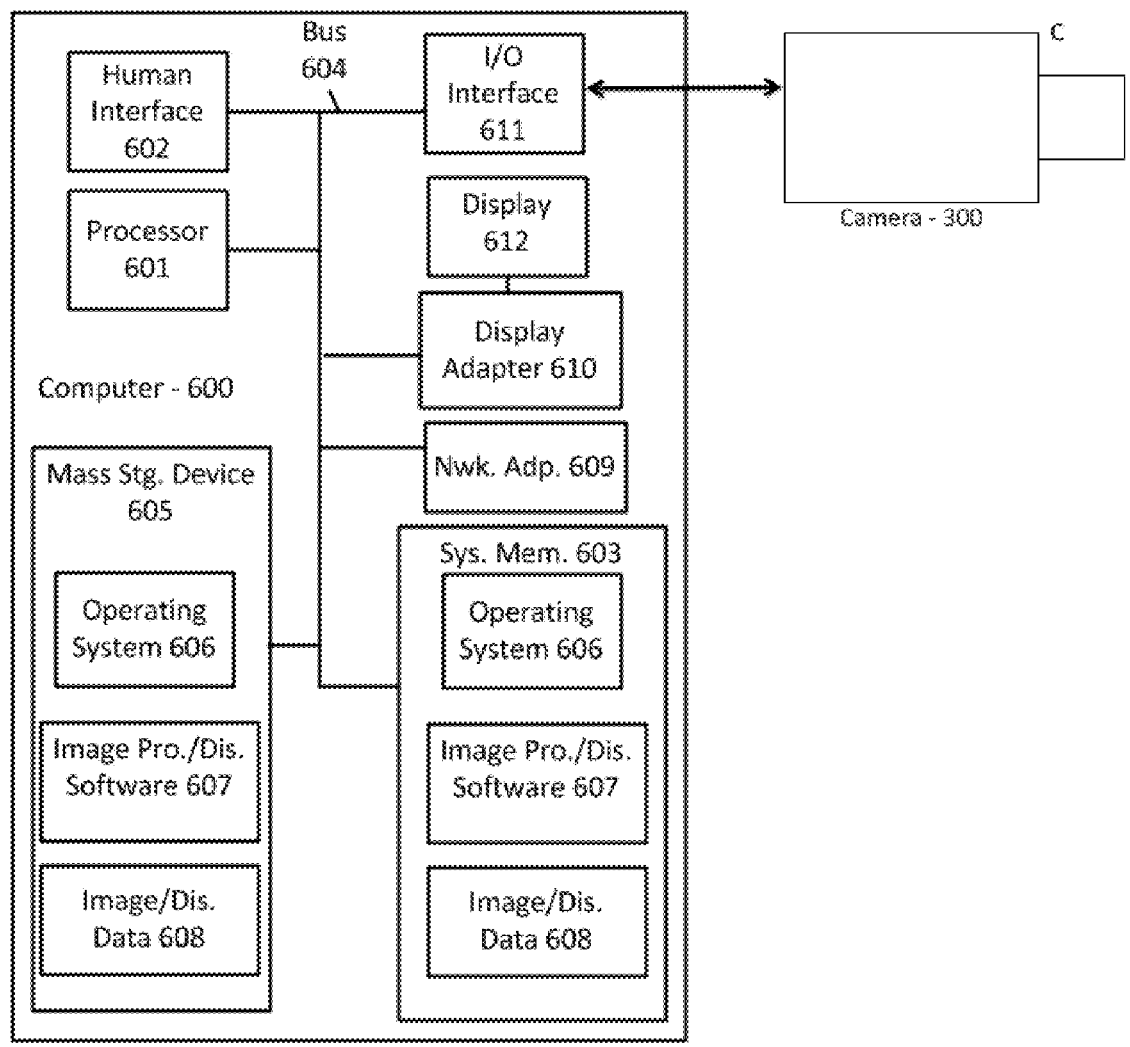
FIG. 8 illustrates a block diagram of a computer and camera according to an aspect of the present invention.
Figure 9A:
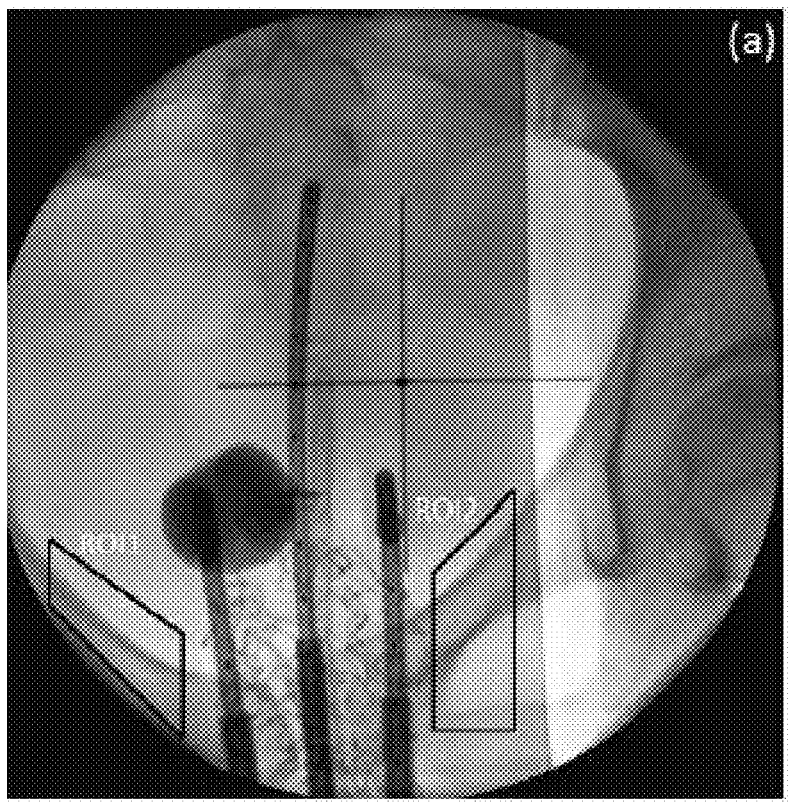
FIGS. 9(a-b) illustrate a reference and a target X-ray images of the applicator within a subject's body before and after the MIll scan respectively.
Figure 9B:
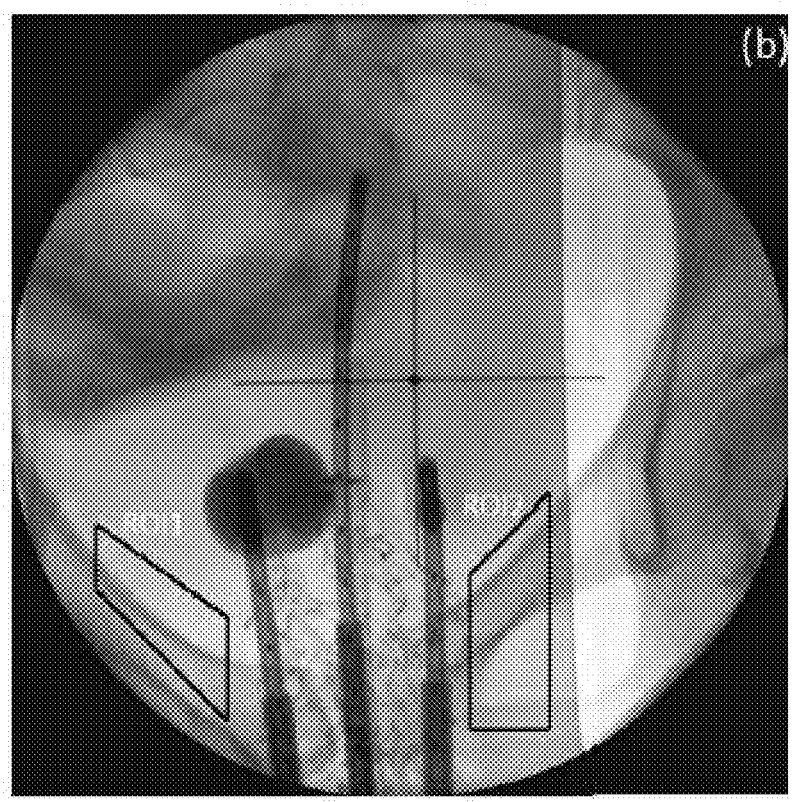
Figure 9C:
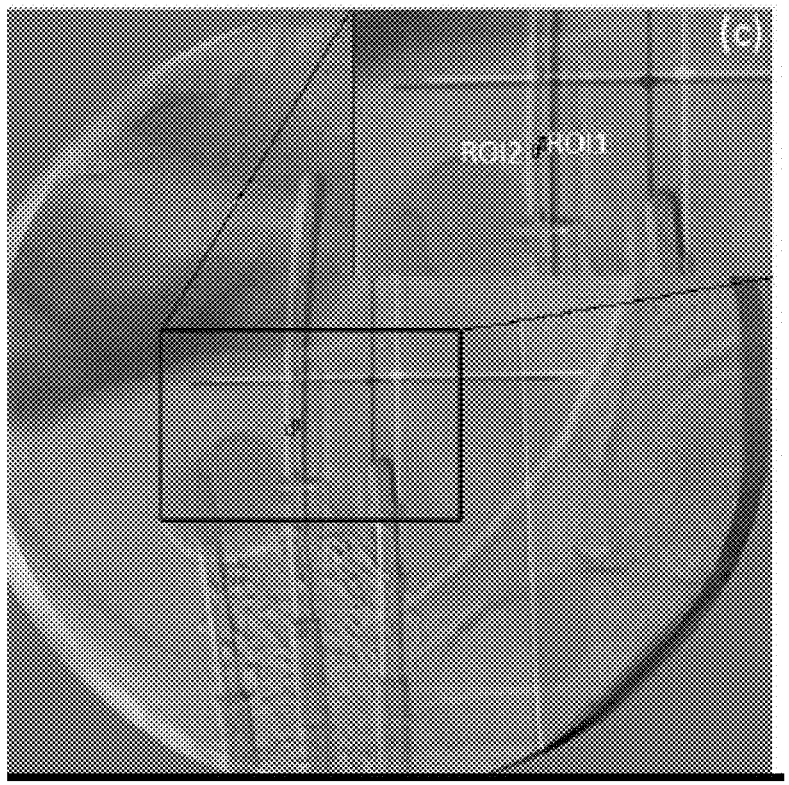
Figure 9D:
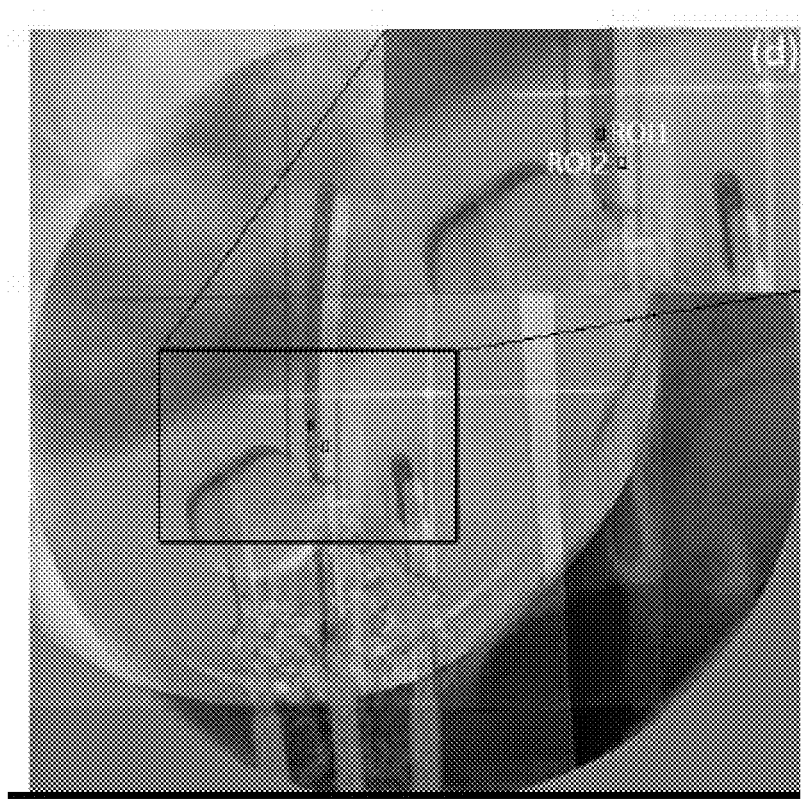

FIG. 8 is a block diagram illustrating a computer 600 that is an exemplary operating environment for performing a portion of disclosed methods according to an embodiment of the present invention. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

Further, one skilled in the art will appreciate that the systems and methods disclosed herein can utilize a general-purpose computing device in the form of a computer 600. The methods discussed above can be performed by the computer 600. For example, the computer 600 performs the duties and responsibilities of the image processing and measuring of displacement as discussed above and below.

The components of the computer 600 can comprise, but are not limited to, one or more processors or processing units 601, a human interface 602, system memory 603, and a system bus 604 that couples various system components including the processor 601 to the system memory 602. In the case of multiple processing units 601, the computer 600 can utilize parallel computing.

The system bus 604 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 604, and all buses specified in this description can also be implemented over a wired or wireless network connection and each of the subsystems, including the processor 601, a mass storage device 605, an operating system 606, image processing and displacement software 607, image and displacement data 608, a network adapter 609, an Input/Output Interface 610, a display adapter 611, and a display device 612.

The computer 600 typically comprises a variety of computer readable media. Exemplary readable media can be any available media that is accessible by the computer 600 and comprises, for example and not meant to be limiting, both volatile and non-volatile media, removable and non-removable media. The system memory 603 comprises computer readable media in the form of volatile memory, such as random access memory (RAM), and/or non-volatile memory, such as read only memory (ROM). The system memory 603 typically contains data such as image and displacement data 608 and/or program modules such as operating system 606 and image processing and displacement software 607 that are immediately accessible to and/or are presently operated on by the processing unit 601.

In another aspect, the computer 600 can also comprise other removable/non-removable, volatile/non-volatile computer storage media. By way of example, FIG. 8 illustrates a mass storage device 605, which can provide non-volatile storage of computer code, computer readable instructions, data structures, program modules, and other data for the computer 600. For example and not meant to be limiting, a mass storage device 605 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 605, including by way of example, an operating system 606 and image processing and displacement software 607. Image and displacement data 608 can also be stored on the mass storage device 604. Image and displacement data 608 can be stored in any of one or more databases known in the art. Examples of such databases include DB2®, Microsoft® Access, Microsoft® SQL Server, Oracle®, mySQL, PostgreSQL, and the like. The databases can be centralized or distributed across multiple systems.

In another aspect, the user can enter commands and information into the computer 600 via an input device (not shown). Examples of such input devices comprise, but are not limited to, a keyboard, pointing device (e.g., a "mouse"), a microphone, a joystick, a scanner, tactile input devices such as gloves, and other body coverings, and the like. These and other input devices can be connected to the processing unit 601 via a human machine interface 602 that is coupled to the system bus 604, but can be connected by other interface and bus structures, such as a parallel port, game port, an IEEE 1394 Port (also known as a Firewire port), a serial port, or a universal serial bus (USB).

In yet another aspect, a display device 612 can also be connected to the system bus 604 via an interface, such as a display adapter 610. It is contemplated that the computer 600 can have more than one display adapter 610 and display device 612. For example, a display device can be a monitor, an LCD (Liquid Crystal Display), or a projector. In addition to the display device 612, other output peripheral devices can comprise components such as the camera 300, speakers (not shown) and a printer (not shown) which can be connected to the computer 600 via Input/Output Interface 611. Any step and/or result of the methods can be output in any form to an output device. Such output can be any form of visual representation, including, but not limited to, textual, graphical, animation, audio, tactile, and the like.

The computer 600 is in communication with the camera(s) 300 of RAPS 100. Here, using the images of the markers 400, 500 and more specifically the reflective surfaces/indicators 422, 522 of each, the image processing and displacement software 607 is able to measure the displacement of the applicator 200 from its original origination within the patient's body 10 based upon the movement (i.e., change in distance) of the patient and applicator markers 400, 500 from their initially captured positions. Applicator motion here refers to the applicator displacement in the cranial-caudal direction. To compute the applicator motion, identification of the reflectors 422, 522 on the patient marker 400 and the applicator marker 500 is performed, and then the distance between the markers 400, 500 is measured calculated from the known geometry (size and spacing) of the patient and applicator reflector means 422, 522. In an aspect, the measurement can be based upon the pixel size captured by the camera(s) 300.

In some cases, the distance between the camera 300 and the marker(s) 400, 500 can have an impact on the measurement. This artifact is more obvious when the surface to marker distance (SMD) is small. However, if the distance between the infrared camera 300 and reflective markers 400, 500 is too close, IR reflection will make it difficult to detect indicators 422, 522 of the markers 400, 500. If the distance is too far, the accuracy of RAPS 100 will suffer. Therefore, it is desirable to place the cameras 300 from the markers 400, 500 at an appropriate distance. In an exemplary aspect, the camera-to-marker distance is fifty centimeters, which results in an accuracy of approximately 0.02 mm. However, other distances can be utilized in other aspects.

According to an aspect, to detect the patient marker 400 and applicator marker 500, the following image processing techniques are used: (1) Edge preserved smoothing: The infrared image is first smoothed with edge preserved smoothing algorithm to preserve edge sharpness while removing image noise. (2) Edge detection: A canny edge detection algorithm is applied to the smoothed image to detect the edges of both markers 400, 500. (3) Morphological image analysis: Morphological analysis is used to reconstruct the patient marker 400 and applicator marker 500 (see FIG. 7(b). (4) Determining pixel size: The centroids of two indicators 522 (when the indicators 522 are circular) of the applicator marker 500 are used to calculate the pixel size with the known physical distance between the indicators 522. (5) Determining applicator motion: The applicator motion is computed by measuring the relative distance change between the center of two centroids of the reflectors 522 of the applicator marker 500 and a centroid of reflector 422 of the patient marker 400. In an aspect, the combination of two infrared cameras 300 and imaging processing and displacement software 607 can make sixty measurements per second, capturing up to 120 frames per second, increasing the real-time reporting, reducing the delay. Such real-time measurement can potentially be used to measure respiratory trace of a patient. The setup above can detect marker motion in 120 Hz, using a fast marker detection algorithm.

In some aspects, as discussed above, a depth camera 300 can be utilized. In such instances, the depth camera 300 is used to measure the orientation of the reflective makers 400, 500 and once their orientation is determined, its angular distance and absolute distance to the imaging center can be computed and used to reduce camera-view effect. However, utilizing two infrared cameras 300 eliminates the camera-view effect.

Phantom Study—Initial

A first phantom study (FIGS. 2 and 5) was performed to compare RAPS measurements with the high accuracy stage. To evaluate the clinical feasibility of the RAPS 100, six cervical cancer patients were enrolled in a clinical trial using MRI-based high-dose-rate brachytherapy with a Tandem-and-Ovoids applicator 200. The results from the RAPS 100 were compared with clinical method, which was validated using registration-based method. The RAPS 100 does not give any radiation dose to patients and it is capable of monitoring the applicator motion at real-time (8 frames per second) with <1 mm accuracy, the infrared markers are also MRI compatible and can be used in modern MM based brachytherapy paradigm.

Applicator Motion Measurements: SA#1

Applicator motion here refers to the applicator displacement in the cranial-caudal direction. To compute the applicator motion, we first identify both applicator markers 500 and the patient markers 400, and then distance between the markers 400, 500 is measured with the pixel size calculated from the known pattern in the applicator marker 500. Among 14 applicator displacements, the maximum difference was 0.8 mm, with the mean value of 0.1 mm and a standard deviation of 0.44 mm. RAPS 100 was able to achieve real-time (4 frames per second) performance using a laptop 600 with Intel Core 2 Dual CPU and 4 Gb of memory. The accuracy is expected to be improved when using a higher resolution infrared camera 300.

System Reproducibility: SA#1

Figure 2:
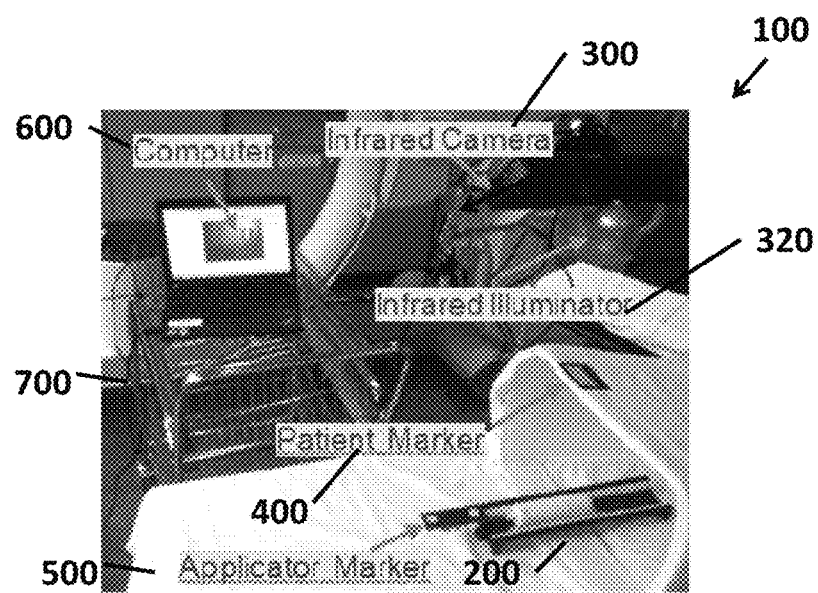
FIG. 2 is the PARS system used in a phantom study according to an aspect of the present invention.
Figure 3:
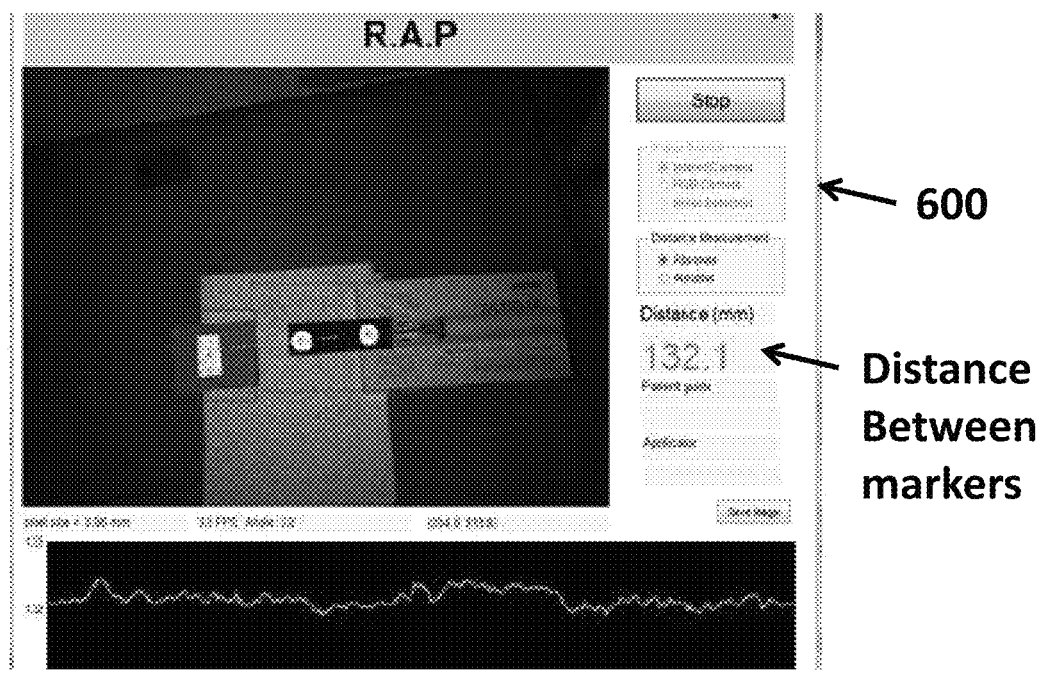
FIG. 3 illustrates a screen capture of the RAPS according to an aspect of the present invention.
Figure 4:
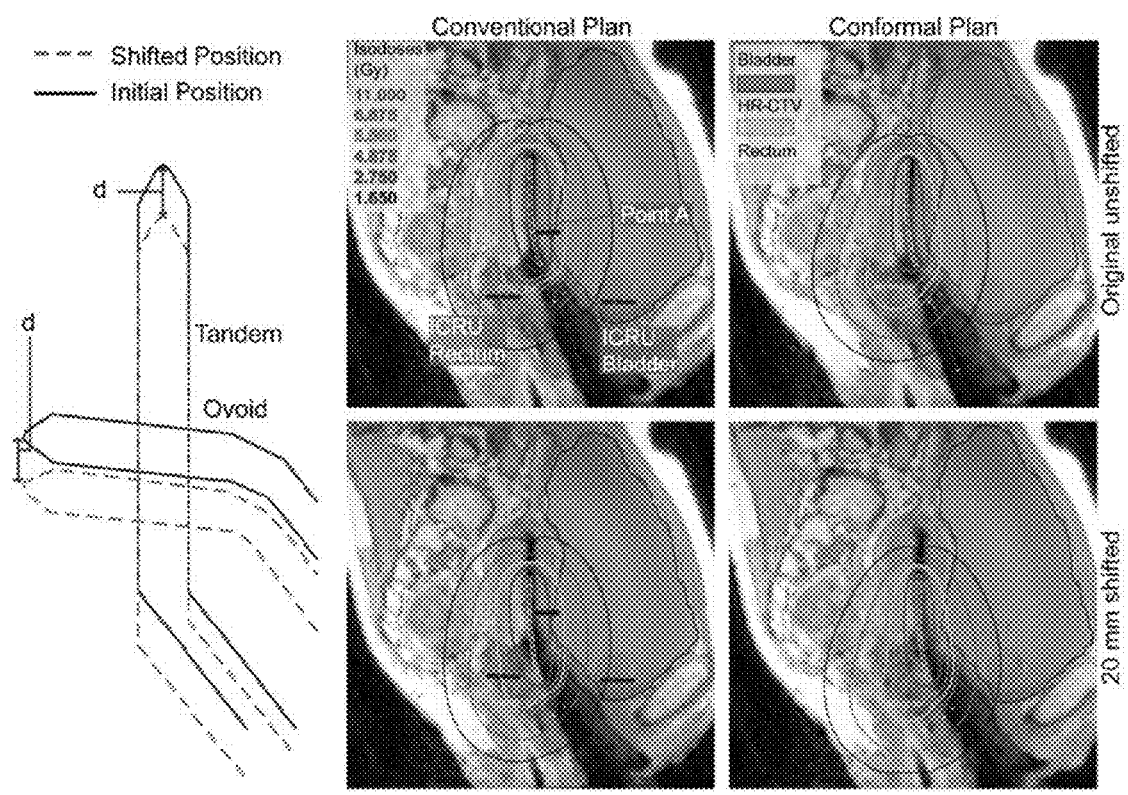
FIG. 4 illustrates simulated tandem and ovoid displacements on a treatment planning system and their resulting isodose lines for conventional, point-A based and MRI-guided, conformal plans.

A phantom study was carried out to measure the accuracy and reproducibility of the RAPS. As seen in FIG. 2, the test phantom consists of a vaginal cylinder applicator 200 with an applicator marker 500 attached, a simulated patient body 10 with a patient marker 500 attached, and a moving track with distance markers (see. FIG. 3). To evaluate system accuracy, the applicator 200 was manually moved on the track between −15 mm and 15 mm. The camera 300 was positioned at approximately 60 cm to the applicator marker 500. A reproducibility test was also conducted by 10 reposition trials. When the camera-to-marker distance was 60 cm, 7 cm uncertainty in a vertical direction introduced 1.0 mm measurement uncertainty. The relative marker positions in the imaging plane can also affect system reproducibility. With one camera 300, the object in the peripheral region will appear to have fewer pixels than that in the central region. This effect can be limited by controlling camera placement geometry. Using this approach, the RAPS 100 reproducibility was within 0.6 mm after 10 reposition trials.

Evaluation of Applicator Displacement Using Currently Available Method: SA #2

Applicator displacements and their dosimetric impacts for cervical cancer brachytherapy were quantified utilizing the currently available method that is orthogonal radiograph. Twenty randomly selected HDR implants were retrospectively examined. Vector distances (d) were measured between each dwell position in the T&O and the center of the bladder foley bulb. The differences (Δd) between d of the pre- and post-X-ray of MM scan were measured. The dosimetric impacts of Tandem & Ovoid (T&O) displacement were measured by virtually displacing the T&O in cranial-caudal directions. Also, dosimetric impacts were measured in conventional, Point-A based plans and MRI-guided, conformal plans. Average T&O displacements due to patient transfer were determined to be Δd=1.3±0.9 mm. Dosimetric impact (avg. 5-6% per 1.5 mm shift) on the rectum (D2cc) was significantly larger ($p<0.028$) than those of the other HR-CTV or OAR. MRIG-CBT plans demonstrate significantly larger dosimetric changes on sigmoid ($p<0.0005$), bladder ($p<0.0001$), HR-CTV ($p<0.0036$), and point A ($p<0.0015$) than those of point A based plans.

Phantom Study 2

Figure 6A:
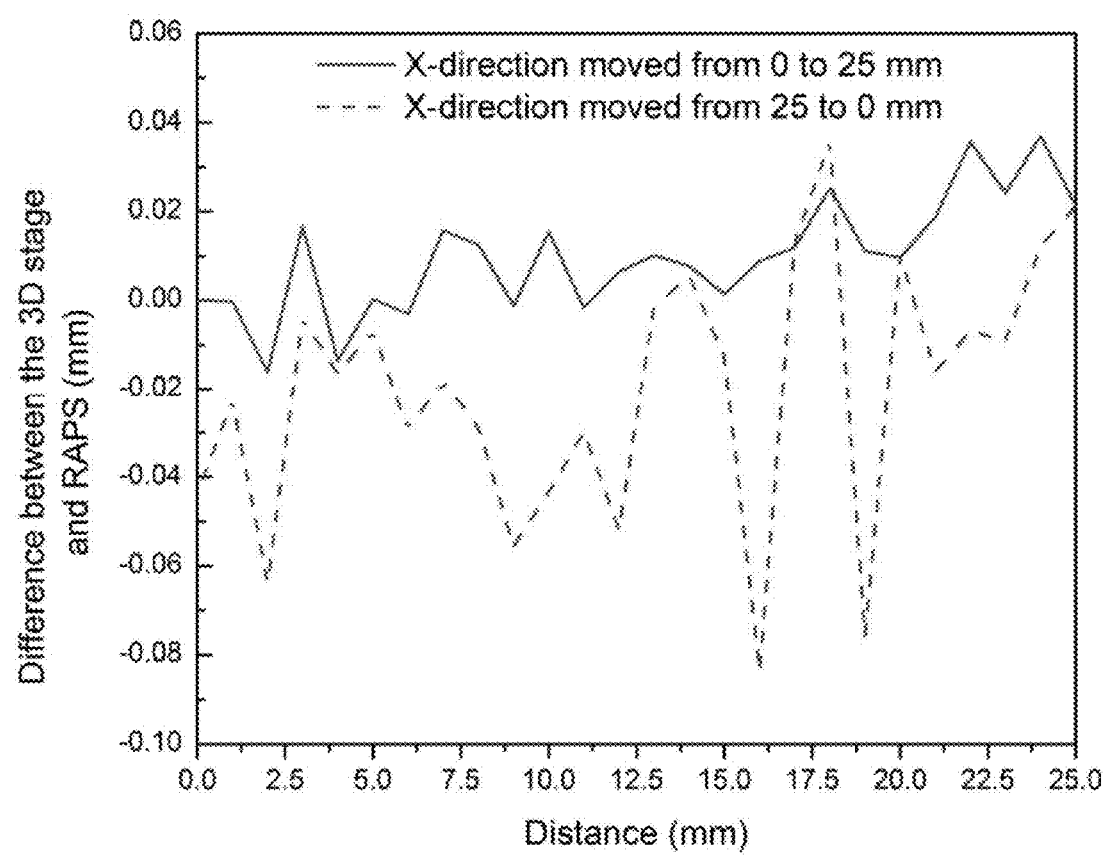
FIGS. 6(a) through 6(c) illustrate the measurement difference between the 3D stage and RAPS in the X-direction, the Y-direction and the Z-direction from the RAPS phantom study of FIG. 5.
Figure 6B:
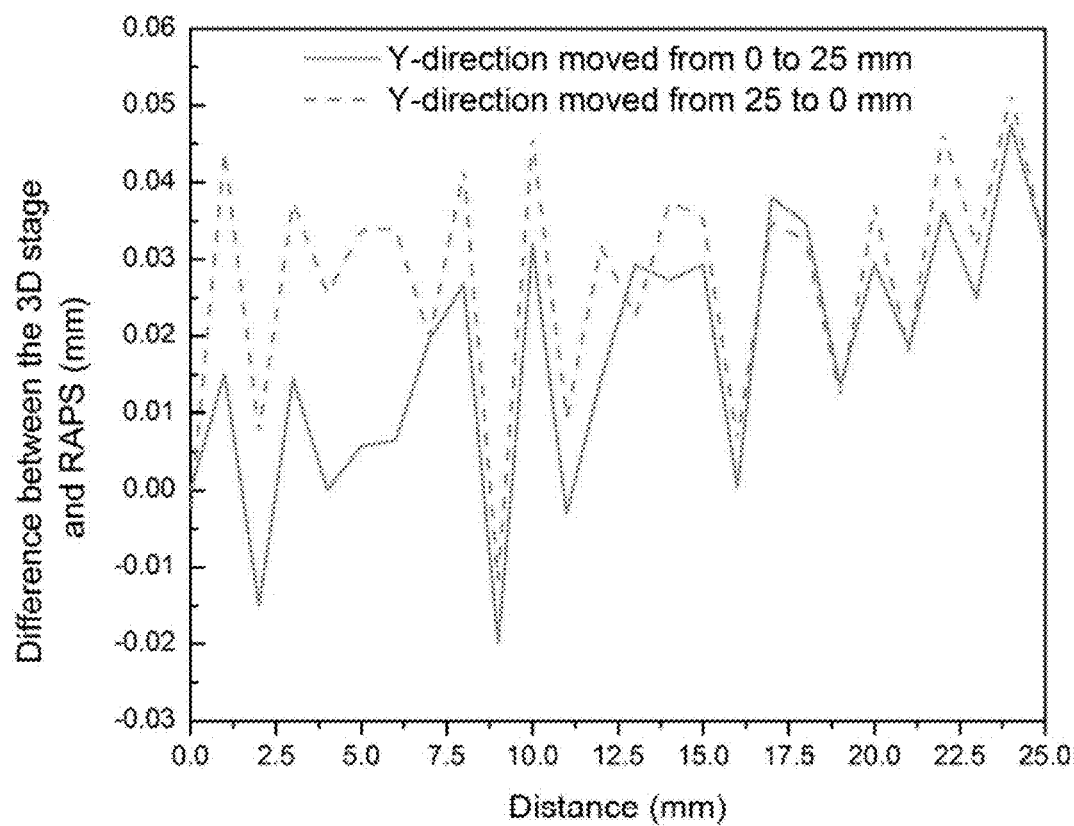
Figure 6C:
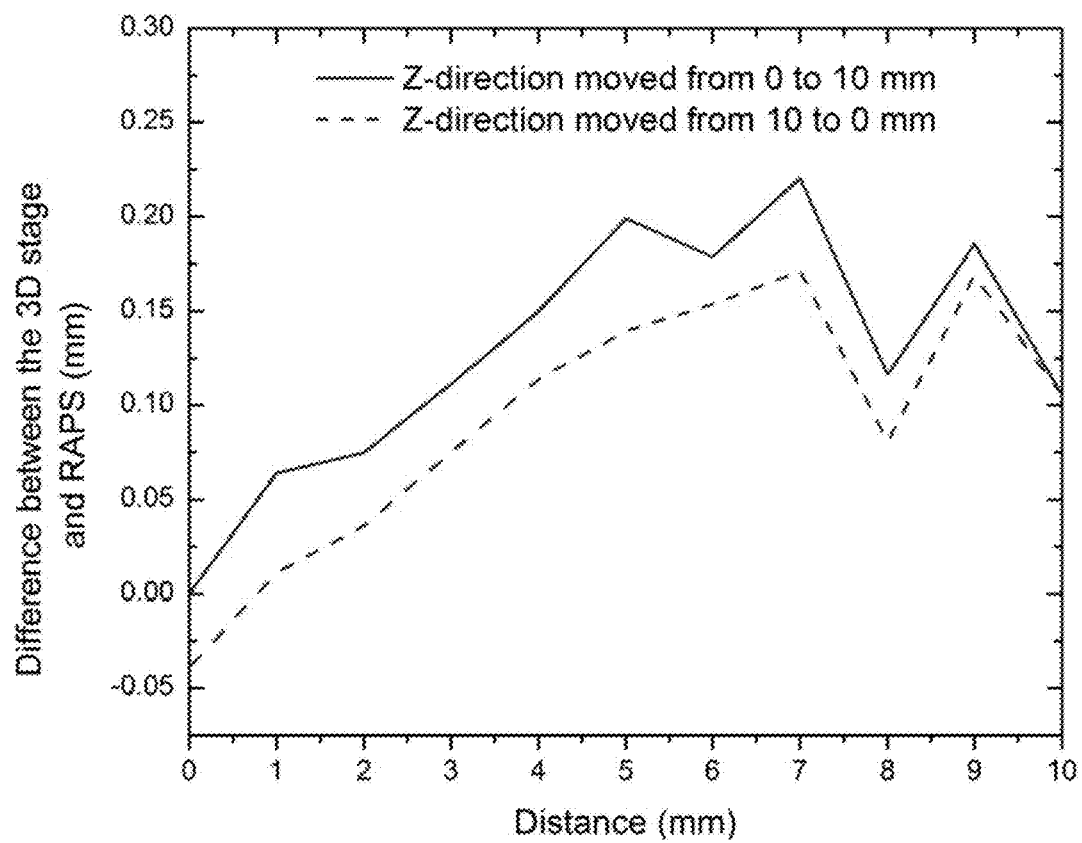

A second phantom study, using two cameras (FIGS. 5 and 7a-c), was performed to compare measurements provided by the RAPS 100 with known displacements from a 3D stage (0.03 mm accuracy in X, Y and Z directions). An IR stereo-camera 300 was attached to a tripod and positioned vertically at 50 cm from the patient marker (FIG. 5). The patient marker 400 was attached to the 3D stage to move it in three directions as indicated by the arrows in FIG. 5. In X and Z directions, the patient marker 400 was moved from 0 to 25 mm, then back to 0 mm with a 1 mm interval (FIGS. 6(a & c)). In the Y direction, the patient marker 400 was moved from 0 to 10 mm, then back to 0 mm with a 1 mm interval (FIG. 6(b)).

Figure 7:
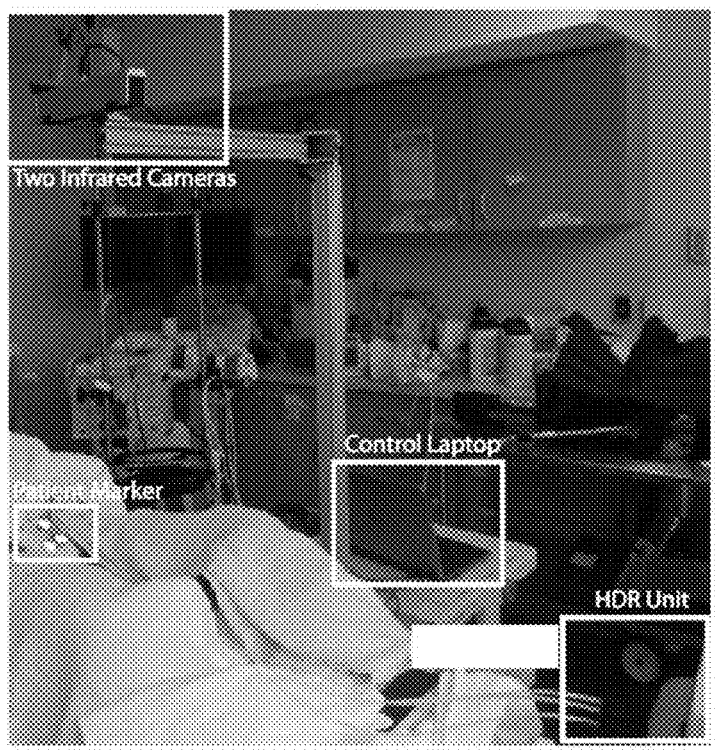
FIG. 7 illustrates an implementation of the RAPS in a clinical trial set up according to an aspect of the present invention.
Figure 7A:
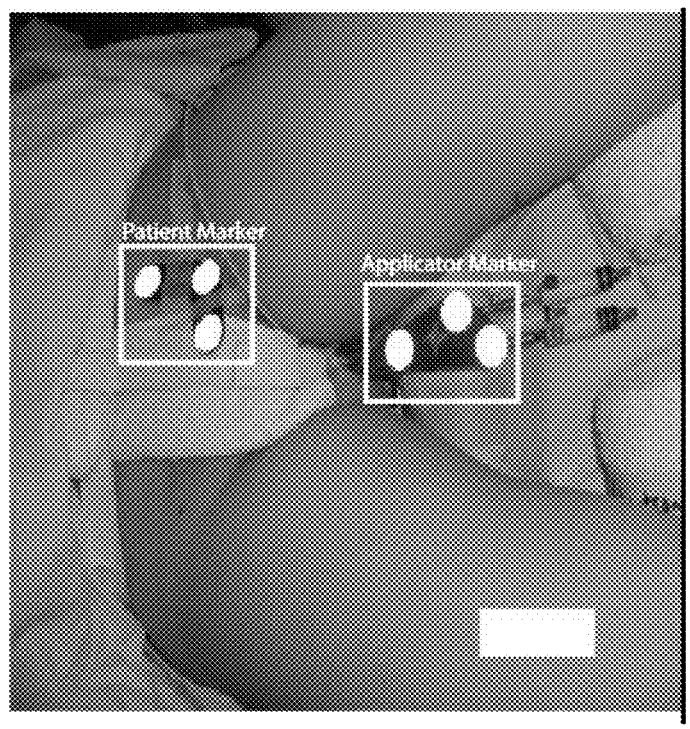
FIGS. 7(a) and 7(b) illustrate a patient marker setup and a screen capture of the RAPS software interface in the clinical trial set up from FIG. 7.
Figure 7B:
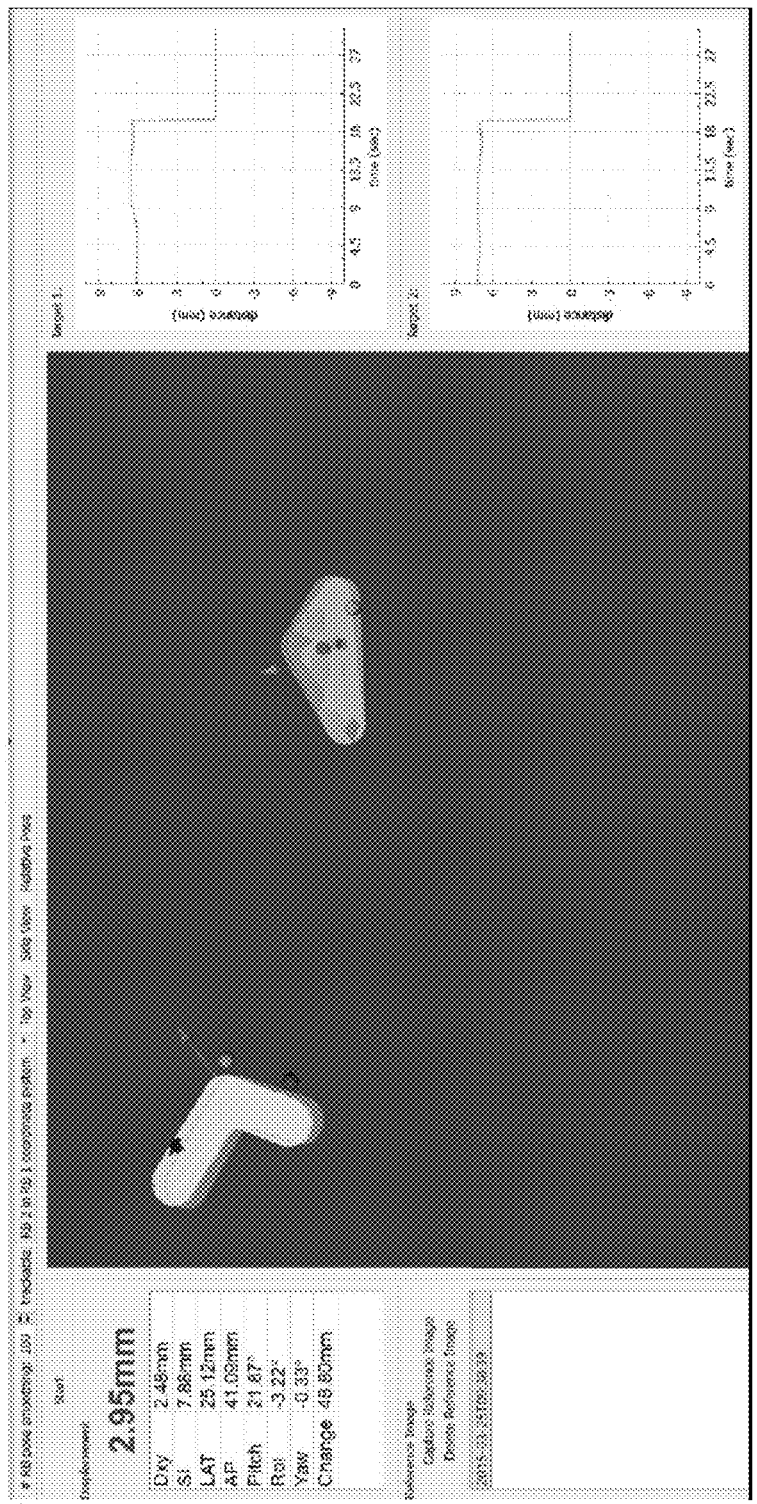

The RAPS 100 was developed to monitor real-time applicator position without additional radiation dose. As illustrated in FIGS. 5(b-c), 7, and 7(a-b), the RAPS 100 includes a calibrated infrared stereo-camera setup 300 a control laptop/computer 600, two custom-designed tracking targets 400, 500, and image processing and displacement software. In an aspect, each tracking target 400, 500 consists of three circular, infrared reflective indicators 422*a/b/c*, 522*a/b/c* with a diameter of 2.5 cm. Two Infrared (IR) cameras 300 (NaturalPoint Inc., Corvallis, Oreg.) with a resolution of 640×480 pixels and rate of 120 frames per second were used to track the markers 400, 500. The RAPS 100 measures applicator movement in real-time by computing the relative displacement between the two tracking targets 400, 500 (see FIG. 7(*b*)), the applicator marker 500 attached to the applicator 200 and the patient marker 400 to the skin in the anterior pelvic region of the patient (FIG. 7(*a*)). Both markers 400, 500 were designed for optimal tracking performance, and to be easily attached to a Fletcher-Suit-Delclos titanium tandem and ovoid's applicator (Varian Medical System, Palo Alto, Calif.). The RAPS 100 is suitable for both CT and magnetic resonance imaging (MRI)-guided HDR BT. FIG. 7(*b*) shows the user interface 612 of the RAPS real-time image processing and displacement software 607. Reconstructed position in real-time of the markers 400, 500 is shown in the center panel; change in applicator pose relative to a reference constellation is shown in the top left panel. Graphs of the absolute displacement of the two markers 400, 500 relative to the recorded reference position (distance measurements) are seen in the top right and lower right position of the RAPS graphical interface. The left lower panel allows a user to capture a reference image. In the center 3D view, the markers 400, 500 can be shown in two different positions simultaneously—the reference position and the current position. As shown, the gray objects correspond to the markers 400, 500 at a reference position whereas the colored objects correspond to the markers in the current position. When using an IR stereo-camera 300, applicator and patient marker configurations have to be "learned" by the IR system. This step allows the recognition of the target shape and the determination of the local coordinate system for each marker 400, 500. In an aspect, two centroids that correspond to the centroid of each tracking target were used to compute their relative positions.

RAPS Clinical Trial

Prospective clinical trials aim to demonstrate the feasibility of the RAPS system. From January 2015 to August 2015, six patients (14 implant cases) with locally advanced cervical cancer were enrolled in our institutional RAPS clinical trial (IRB#201210832) using MRI-based HDR BT with Tandem-and-Ovoids (T&O) applicators. The median age of the patients was 47 years (range 40-62). Four patients had FIGO stage IIB to IVB, two patients had FIGO stage IIIB/IVB and T1b2N1. Treatment was performed with a Varisource IX brachytherapy afterloader (Varian Medical System, Palo Alto, Calif.) with an Iridium-192 source. Each patient underwent orthogonal planar X-ray images consisting of anterior-posterior (AP) and lateral projections with the applicator in place. Orthogonal X-ray images were acquired both before and after patient transfer to the MR imaging room in order to measure potential applicator displacement.

Applicator position was verified using radiopaque dummy wires that were placed into the T&O applicator. The distance between two consecutive radiopaque markers on the dummy wire is 10 mm. X-ray images have a size of 1024×1024 pixels with a pixel resolution of 0.14×0.14 mm$^2$ and were acquired using the same imaging protocol.

Applicator Displacement Using Applicator Position Monitoring System (RAPS)

The applicator displacement was measured using RAPS (FIG. 7). The patient marker was attached to the patient's skin surface and the applicator marker was firmly attached to the HDR BT applicator (FIG. 7(*a*)). The RAPS software 697 reported real-time applicator displacement measurements in the superior-inferior direction (FIG. 7(*b*)).

Applicator Displacement Using X-ray Images

In the clinical method, a medical physicist calculated the applicator displacement (superior-inferior direction) by measuring the difference in distance from the pelvic bone to the corresponding dummy markers in two X-ray images.

To validate our clinical method, we compared it to registration-based method. For each patient, two AP pelvis images were fused semi-automatically using the rigid image registration algorithm from MIPAV (National Institutes of Health, U.S.). The first X-ray image (FIG. 9(*a*)), taken before the 3D imaging scan, was used as the reference image, and the second X-ray image (FIG. 9(*b*)), taken after 3D imaging scan was registered with the reference image using bony anatomy rigid registration. Rigid registration with three degrees-of-freedom was chosen to better align the rigid structures (pelvic bone) in 2D images. Two regions of interest, including the structures to the left and right of the bony anatomy (FIGS. 9(*a*-*b*)), were used in the registration process.

The intensity-based registration procedure maximizes similarity measurement based on normalized cross-correlation. The optimal rigid alignment of the bony anatomy is found by maximizing the normalized cross-correlation value, which ranges from 0 (bad alignment) to 1 (good alignment). The method is evaluated at multiple resolutions, starting with the lowest resolution. Powell's method was used as the optimization method for maximization of the similarity measure. The registered image is obtained from the optimal rigid transformation that aligns the bony anatomy of the target image (FIG. 9(*b*)) to the reference image (FIG. 9(*a*)). The registered image, which overlaps the reference image (FIG. 9(*c*)), was used to measure applicator displacement by comparing the position of the dummy markers relative to the bony anatomy. Image registration was visually verified by alignment to the pelvic bone (FIG. 9(*c*)).

To compute the applicator displacement in the superior-inferior direction, a ROI-based method was developed using MATLAB (Mathworks, MA, USA). First, a canny edge detection algorithm is applied to detect the edges of the dummy markers. Then, masks were created from two rectangular regions of interest (ROIs) delineating dummy markers in the reference image and the registered image (FIG. 9(*c*)). The applicator displacement is computed by measuring the absolute difference in the centroids position of the ROIs in the two images (FIG. 9(*d*)).

Results

To evaluate the efficacy and feasibility of RAPS 100 in the clinical trial, we compared RAPS measurements to applicator displacement measurements obtained using the clinical method. The absolute average difference between RAPS and the clinical method was 1.46±1.13 mm with a maximum difference of 3.71 mm (FIG. 10(*a*)). Absolute average difference between the clinical method and registration-based method was 0.49±1.13 mm with a maximum difference of 0.86 mm (FIG. 10(*b*)). In the phantom study, the average difference between RAPS measurements and the 3D stage was 0.02±0.02 mm in the X-direction (FIG. 6(*a*)), 0.11±0.06 mm in the Y-direction (FIG. 6(*b*)) and 0.02±0.01 mm in the Z-direction (FIG. 6(*c*)).

When the RAPS 100 setup was used in our clinic, a maximum applicator displacement of 6.66 mm was observed. For all T&O implant cases, an absolute average applicator displacement of 2.0±1.5 mm was observed in the superior-inferior direction (FIG. 10(c)). An absolute average displacement in the applicator position of 1.64±1.63 mm (range: 0 mm-5.20 mm) was observed using the clinical method, 1.74±1.37 mm using the registration-based method.

Figure 10A:
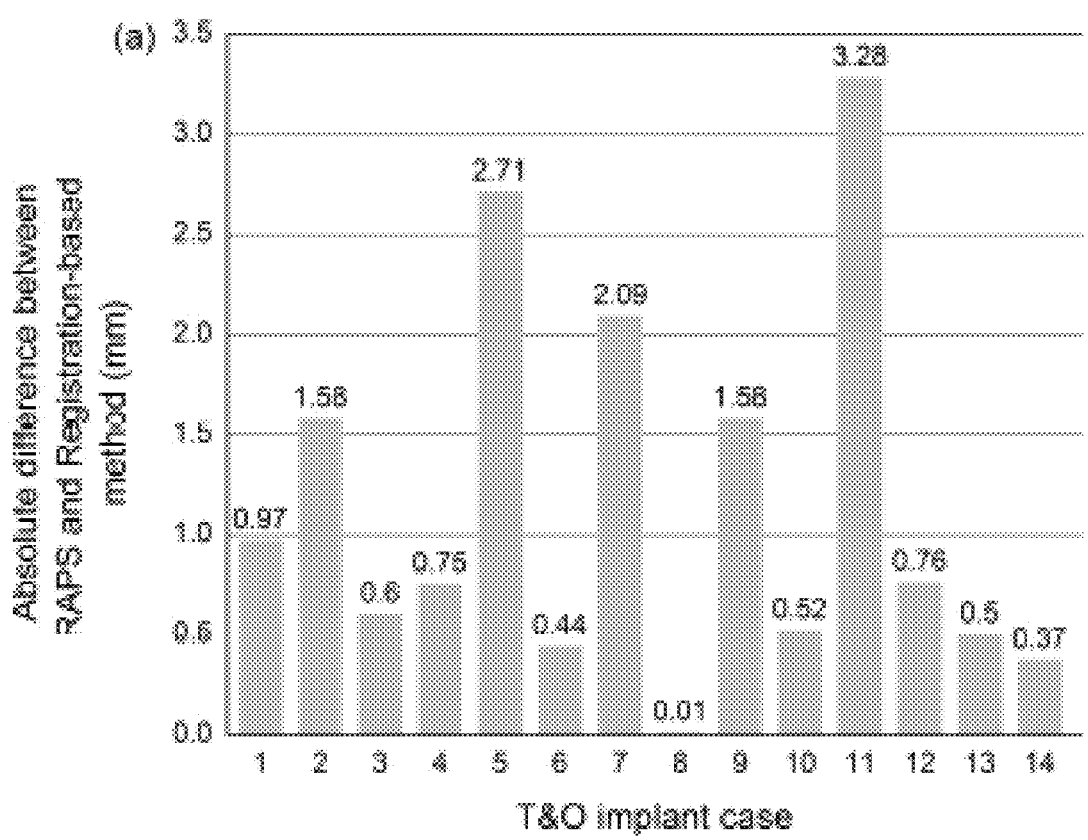
FIGS. 10 (a-d) are graphical representations of the absolute displacements of applicators (a) between the RAPS and clinical method; (b) between clinical method and registration-based method; (c) the RAPS measurement of applicator displacements for all cases; and (d) Applicator displacement during HDR BT delivery for all cases. Data in case 1, 4 and 10 were not available.
Figure 10B:
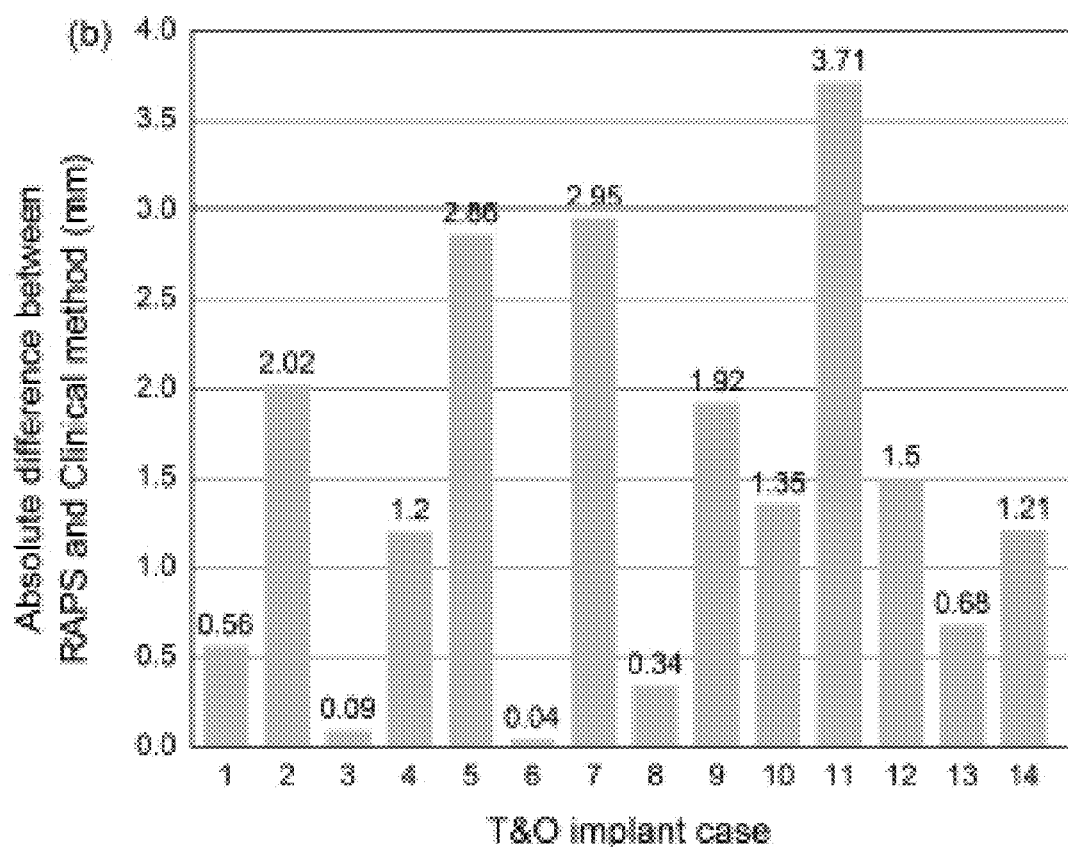
Figure 10C:
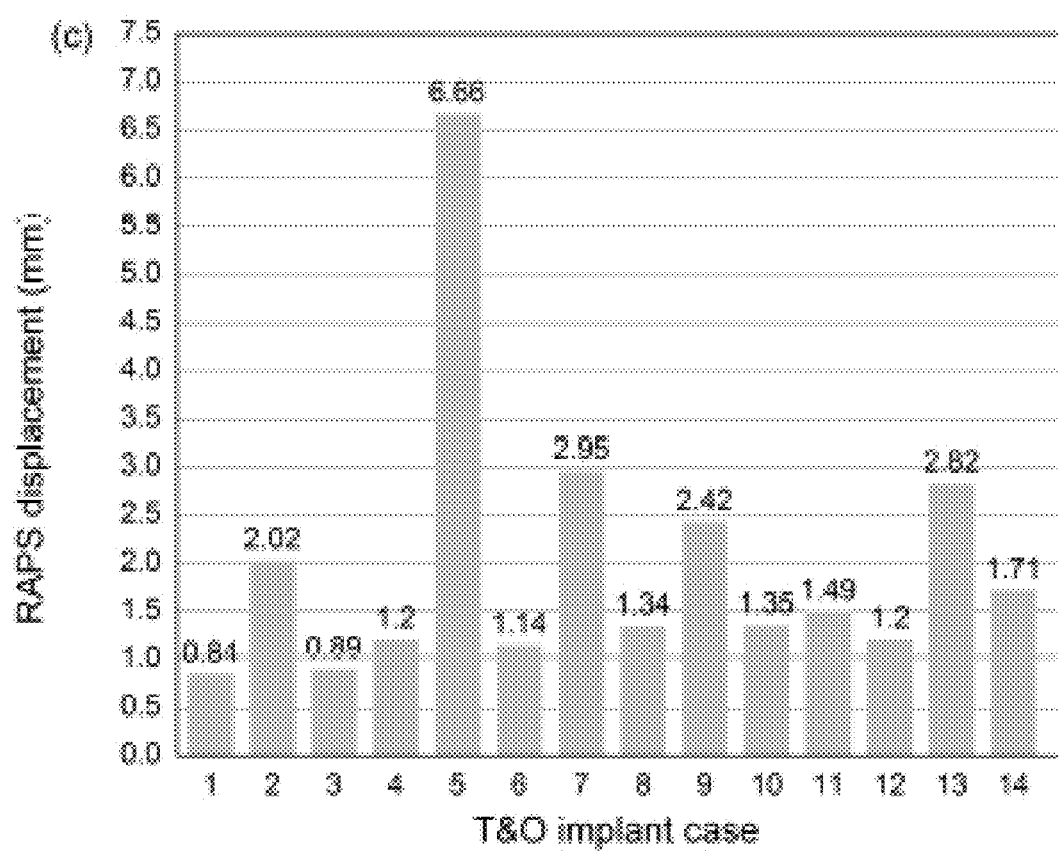
Figure 10D:
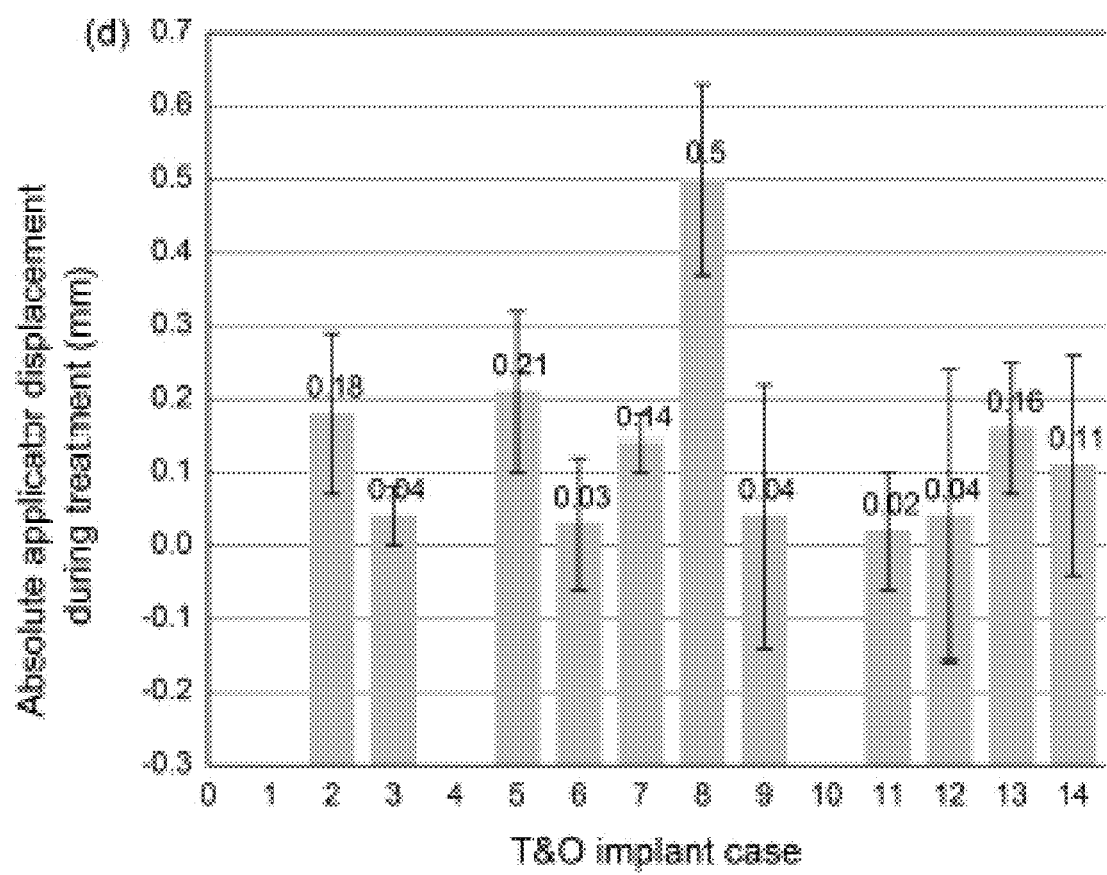
Figure 11A:
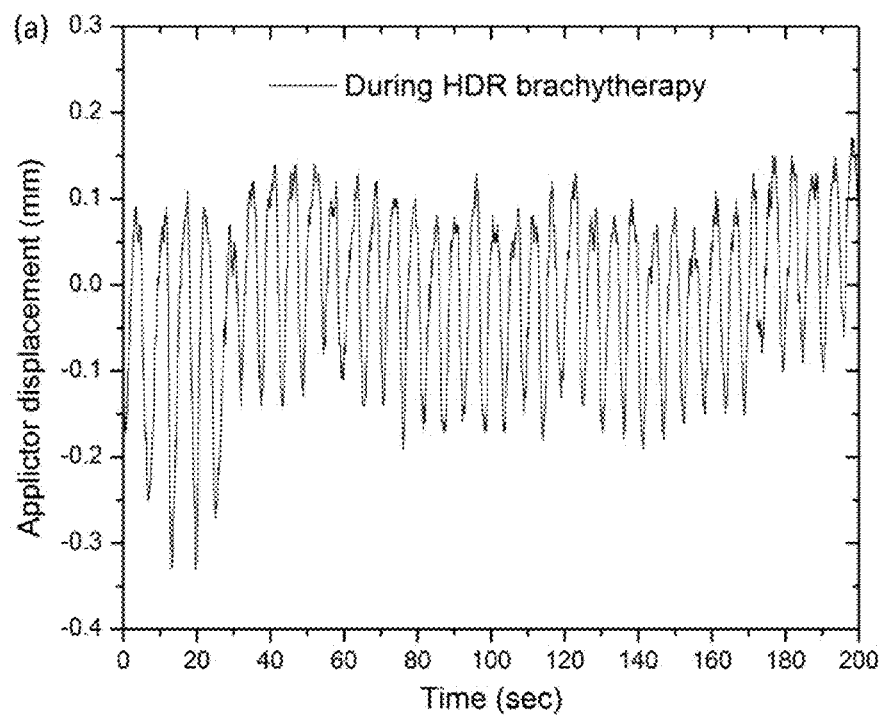
FIGS. 11(a-b) illustrate graphical representations of (a) time-series data of the patient marker movement during T&O HDR treatment delivery for one T&O implant case and (b) FFT of the time-series data.
Figure 11B:
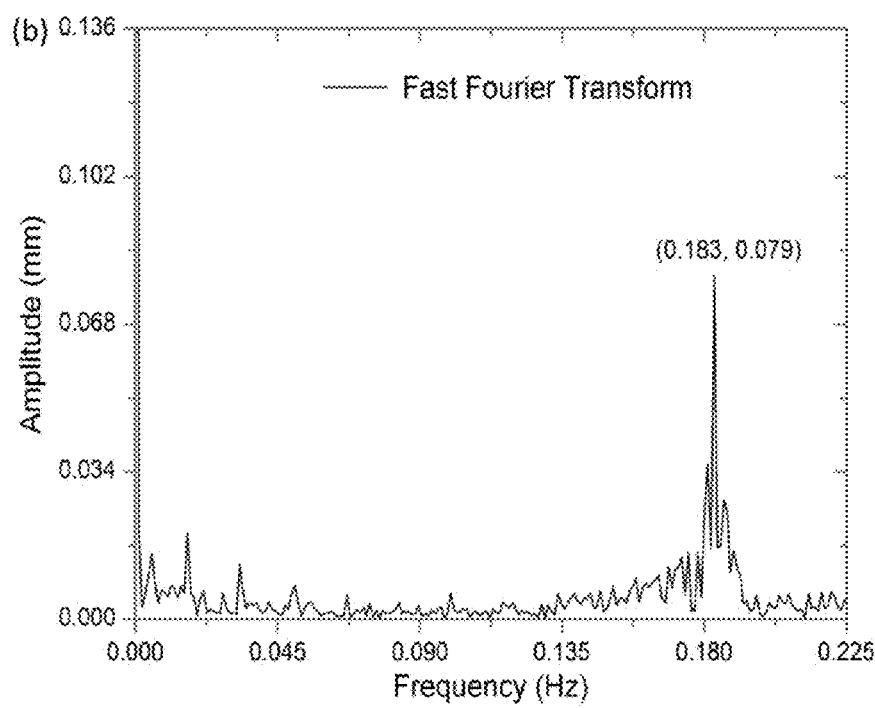

Using RAPS, the average applicator displacement during HDR treatment was 0.13±0.11 mm (FIG. 10(d)). Respiratory motion had a minimal impact on RAPS measurements in the superior-inferior direction. Even though the magnitude of the respiratory motion is less than 0.2 mm, for certain patients, we were able to measure the respiratory rate using the Fast Fourier Transform (FFT) of the time-series data during HDR treatment (FIG. 11(a)). As shown in FIG. 11(b), the peak frequency corresponds to a respiratory rate of 11 breaths/min. The phantom study indicated the accuracy of RAPS with a mean accuracy of 0.02±0.01 mm in the superior-inferior direction (FIG. 6(c)), 0.02±0.02 mm in lateral direction (FIG. 6(a)), and 0.11±0.06 mm in anterior-posterior direction (FIG. 6(b)). However, we observed inconsistent RAPS measurements at the beginning of the clinical study. This inconsistency was caused by the location and orientation of the markers in the patient marker setup (FIG. 7(a)), which affected the local coordinate system. To solve this problem, a calibration method was developed in the image processing and displacement software 607 that assures that IR markers 400, 500 always get the same local coordinate system assigned. Since the software update, RAPS 100 provides more stable and consistent results. To measure applicator displacement, some authors used registration of the bony anatomy on CT or MR scans. De Leeuw et al. registered two MR scans using a full grey-value mutual information registration and found an average applicator displacement of 3-4 mm in the cranial direction. The authors did not insert dummy markers into the applicator but used the visible black signal voids of the applicator where the authors defined two marker points at the tip and base of the tandem. In our study, we registered two x-ray images (before and after the MR scan) with dummy markers using rigid registration of the bony anatomy and so obtained an absolute average displacement in the applicator position of 1.74±1.37 mm. Also, we found an absolute average displacement of 1.64±1.63 mm using the clinical method. However, there are few factors that may affect measurements using the clinical method and registration-based method:

1. Change of the x-ray source position. During x-ray imaging, the change in the field of view due to the position of the X-ray source and related couch position will affect the apparent position of the markers in relation to the bony anatomy. At the correct X-ray tube position (FIG. 9(c)), applicator displacement was 1.0 mm using the clinical method. At varying X-ray tube positions (FIG. 9(d)), applicator displacement was of 4.7 mm using the clinical method. To minimize the impact of x-ray source position, we marked the laser position of the x-ray source position on the patient's skin after the first X-ray image is acquired and aligning the laser to the skin marks when acquiring the second X-ray image.

2. Reproducibility of the dummy wire placement. Due to MR incompatibility, the dummy marker wire was removed before the MR scan and reinserted after the MR scan, which can introduce additional uncertainties in dummy marker positioning.

3. Selection of the region of interest. Areas delineated by regions of interest should include most of the common structures in the two X-ray images to improve alignment quality of the bony anatomy and reduce registration errors.

In all cases, the average difference between the RAPS 100 and clinical method were within 1.5 mm. Also, the average difference between the clinical method and registration-based method were within 1.0 mm. In implant #5, we observed an applicator displacement of 6.66 mm using RAPS and 3.80 mm using the clinical method. This difference could be due to the change in the orientation of the patient marker 400 during the real-time tracking procedure. During clinical trials the patient marker 400 was attached to the patient's skin where breathing motion may have affected the results. However, we observed an average breathing motion of 0.13 mm with a standard deviation of 0.11 mm. A single peak corresponding to the frequency of breathing motion was observed in one case (FIG. 11(b)). For other implant cases, we did not observe this peak, which may be due to noise in the trace signal and to patient marker that was attached at different locations on patient skin. The small average displacements during T&O HDR BT treatment indicates a minimal impact of the breathing motion on the applicator displacement measurements obtained by the RAPS 100 in the superior-inferior direction. Breathing motion most likely occurs in the anterior-posterior direction, limiting applicator displacement that occurs in the superior-inferior direction.

RAPS 100 has minimum clinical impact with respect to the procedure time increase. Under current clinical workflow, it took less than 5 minutes to setup the RAPS 100, including attaching the patient and applicator markers 400, 500, and capturing the reference measurements. The RAPS 100 demonstrates the feasibility of detecting applicator displacement in real-time.

Up to 6.66 mm applicator displacement (avg. 2.0±1.5 mm) was recorded on RAPS 100 during a patient transfer for a 3D image scan. In the clinical trial, average applicator displacement differences between RAPS and the clinical method were within 1.5 mm. In the phantom study, RAPS 100 measurement was within 0.2 mm. During T&O HDR treatment delivery, a small displacement was observed in the superior inferior direction (0.13±0.11 mm) indicating that RAPS 100 results were not affected by breathing motion.

RAPS has distinctive advantages: 1) real-time continuous monitoring; 2) no radiation dose to patients; 3) very affordable; 4) self-calibration, additional camera calibration procedure is required; 5) MRI compatible.

RAPS 100 will enable more patients to get the benefits of 3D imaging guidance for their intracavitary brachytherapy without increase in dosimetric uncertainties due to a patient transfer. It will also improve the physician's confidence in delivering 3D conformal BT. 3D imaging based contouring of the organs-at-risk (OAR) during each fraction of brachytherapy is one noninvasive method of accurately determining the doses received by determined volumes in addition to points. Advantages of 3D imaging in intracavitary brachytherapy that may lead to improved patient outcome, irrespective of the dose rate. For instance, 3D imaging guided GYN brachytherapy can allows to avoid or early detect a uterine perforation, ensuring target coverage, and avoiding excessive dose to the OAR.

Having thus described exemplary embodiments of a method to produce metallic composite material, it should be noted by those skilled in the art that the within disclosures are exemplary only and that various other alternatives, adaptations, and modifications may be made within the scope of this disclosure. Accordingly, the invention is not limited to the specific embodiments as illustrated herein, but is only limited by the following claims.

The following references are relevant to the subject matter disclosed above.

Gerszten K, Paul C, Kin G, Mogus R, Sonnik D Kalend A. High dose rate tandem and ring applicator movement with patient transfer from simulation to treatment room. Journal of Brachytherapy International 1998; 14:15-20.

Haie-Meder C, Potter R, Van Limbergen E, et al. Recommendations from gynaecological (GYN) GEC-ESTRO Working Group (I): concepts and terms in 3D image based 3D treatment planning in cervix cancer brachytherapy with emphasis on MRI assessment of GTV and CTV. Radiother Oncol 2005; 74:235-245.

Hellebust T P, Kirisits C, Berger D, et al. Recommendations from gynaecological (GYN) GECESTRO working group: considerations and pitfalls in commissioning and applicator reconstruction in 3D image-based treatment planning of cervix cancer brachytherapy. Radiother Oncol 2010; 96:153-160.

Kim Y, Huang Y, Chesnut D, Sangster N Oldham A. Applicator Displacements for Cervical Cancer Brachytherapy Due to Additional Scan for 3D Image Guidance. Radiother Oncol 2011; 99:5257-258.

Potter R, Georg P, Dimopoulos J C, et al. Clinical outcome of protocol based image (MRI) guided adaptive brachytherapy combined with 3D conformal radiotherapy with or without chemotherapy in patients with locally advanced cervical cancer. Radiother Oncol 2011; 100:116-123.

Potter R, Haie-Meder C, Van Limbergen E, et al. Recommendations from gynecological (GYN) GEC ESTRO working group (II): concepts and terms in 3D image-based treatment planning in cervix cancer brachytherapy-3D dose volume parameters and aspects of 3D image-based anatomy, radiation physics, radiobiology. Radiother Oncol 2006; 78:67-77.

Schindel J, Zhang W, Anderson J, Bhatia S K, Sun W Kim Y. Evaluations on applicator displacements of 3D image-guided brachytherapy for cervical cancer due to a patient movement for 3D imaging. Brachytherapy 2013; (Submitted).

Tanderup K, Hellebust T P, Lang S, et al. Consequences of random and systematic reconstruction uncertainties in 3D image based brachytherapy in cervical cancer. Radiother Oncol 2008; 89:156-163.

Tanderup K, Hellebust T P, Lang S, et al. Consequences of random and systematic reconstructionuncertainties in 3D image based brachytherapy in cervical cancer. Radiother Oncol 2008; 89:156-163.

Viswanathan A N, Beriwal S, De Los Santos J F, et al. American Brachytherapy Society consensus guidelines for locally advanced carcinoma of the cervix. Part II: high-dose-rate brachytherapy. Brachytherapy 2012; 11:47-52.

Viswanathan A N Erickson B A. Three-dimensional imaging in gynecologic brachytherapy: a survey of the American Brachytherapy Society. Int J Radiat Oncol Biol Phys 2010; 76:104-109.

Viswanathan A N, Thomadsen B Committee ABSCCR. American Brachytherapy Society consensus guidelines for locally advanced carcinoma of the cervix. Part I: general principles. Brachytherapy 2012; 11:33-46.

Potter R, Georg P, Dimopoulos J C, et al. Clinical outcome of protocol based image (MRI) guided adaptive brachytherapy combined with 3D conformal radiotherapy with or without chemotherapy in patients with locally advanced cervical cancer. *Radiother Oncol* 2011; 100:116-123.

Nkiwane K S, Potter R, Fokdal L U, et al. Use of bladder dose points for assessment of the spatial dose distribution in the posterior bladder wall in cervical cancer brachytherapy and the impact of applicator position. *Brachytherapy* 2015; 14:252-259.

Schindel J, Zhang W, Bhatia S K, et al. Dosimetric impacts of applicator displacements and applicator reconstruction-uncertainties on 3D image-guided brachytherapy for cervical cancer. *J Contemp Brachytherapy* 2013; 5:250-257.

Gerszten K, Paul C, Kin G. High dose rate tandem and ring applicator movement with patient transfer from simulation to treatment room. *J Brachytherapy Int.* 1998; 14:15-20.

Hoskin P J, Cook M, Bouscale D, et al. Changes in applicator position with fractionatedhigh dose rate gynaecological brachytherapy. *Radiother Oncol* 1996; 40:59-62.

Datta N R, Kumar S, Das K J, et al. Variations of intracavitary applicator geometry during multiple HDR brachytherapy insertions in carcinoma cervix and its influence on reporting as per ICRU report 38. *Radiother Oncol* 2001; 60:15-24.

Damato A L, Cormack R A, Viswanathan A N. Characterization of implant displacement and deformation in gynecologic interstitial brachytherapy. Brachytherapy 2014; 13:100-109.

Tanderup K, Hellebust T P, Lang S, et al. Consequences of random and systematic reconstruction uncertainties in 3D image based brachytherapy in cervical cancer. *Radiother Oncol* 2008; 89:156-163.

De Leeuw A A, Moerland M A, Nomden C, et al. Applicator reconstruction and applicator shifts in 3D MR-based PDR brachytherapy of cervical cancer. *Radiother Oncol* 2009; 93:341-346.

Kim Y, Huang Y, Chesnut D, et al. Applicator displacements for cervical cancer brachytherapy due to additional scan for 3D image guidance. *Radiother. Oncol.* 2011; 99:S257-S258

Yoshida K, Ueda M, Takenaka T, et al. Daily CT measurement of needle applicator displacement during multifractionated high-dose-rate interstitial brachytherapy for postoperative recurrent uterine cancer. *J Radiat Res* 2012; 53:295-300.

Mikami M, Yoshida K, Takenaka T, et al. Daily computed tomography measurement of needle applicator displacement during high-dose-rate interstitial brachytherapy for previously untreated uterine cervical cancer. *Brachytherapy* 2011; 10:318-324.

Shukla P, Chopra S, Engineer R, et al. Quality assurance of multifractionated pelvic interstitial brachytherapy for postoperative recurrences of cervical cancers: a prospective study. *Int J Radiat Oncol Biol Phys* 2012; 82: e617-622.

Bahena J H, Martinez A, Yan D, et al. Spatial reproducibility of the ring and tandem highdose rate cervix applicator. *Int J Radiat Oncol Biol Phys* 1998; 41:13-19. Pham H T, Chen Y, Rouby E, et al. Changes in high-dose-rate tandem and ovoid applicator positions during treatment in an unfixed brachytherapy system. *Radiology* 1998; 206:525-531.

Thomadsen B R, Shahabi S, Stitt J A, et al. High dose rate intracavitary brachytherapy for carcinoma of the cervix: the Madison system: II. Procedural and physical considerations. *Int Radiat Oncol Biol Phys* 1992; 24:349-357.

Milickovic N, Giannouli S, Baltas D, et al. Catheter autoreconstruction in computed tomography based brachytherapy treatment planning. *Med Phys* 2000; 27:1047-1057.

Kirisits C, Rivard M J, Baltas D, et al. Review of clinical brachytherapy uncertainties: analysis guidelines of GEC-ESTRO and the AAPM. *Radiother Oncol* 2014; 110:199-212.

Goyal S, Kataria T. Image guidance in radiation therapy: techniques and applications. *Radiol Res Pract* 2014; 2014: 705604.

Buchali A, Koswig S, Dinges S, et al. Impact of the filling status of the bladder and rectum on their integral dose distribution and the movement of the uterus in the treatment planning of gynaecological cancer. *Radiother Oncol* 1999; 52:29-34.

Xia J, Waldron T, Kim Y. A real-time applicator position monitoring system for gynecologic intracavitary brachytherapy. *Med Phys* 2014; 41:011703.

Sarvaiya J N, Patnaik S, Bombaywala S. Image registration by template matching using normalized Cross-Correlation. *Advances in Computing, Control, & Telecommunication* 2009; 819:28-29.

Grau V, Becher H, Noble J A. Registration of multiview real-time 3-D echocardiographic sequences. *IEEE Trans Med Imaging* 2007; 26:1154-1165.

Powell M. An efficient method for finding the minimum for a function of several variables without calculating derivatives. *Computer J* 1964; 7:155-162

Canny J. A computational approach to edge detection. *IEEE Trans Pattern Anal Mach Intell* 1986; 8:679-698.

What is claimed is:

1. A real-time applicator monitoring system for use in HDR brachytherapy, comprising:
   a. at least two markers, comprising a first marker and a second marker, wherein the first marker is configured to be attached to a brachytherapy applicator and the second marker is configured to be attached to a patient;
   b. at least one camera configured to capture images of the at least two markers in relation to one another; and
   c. a computer in communication with the at least one camera, the computer comprising memory and a processor, wherein the processor is configured to continuously monitor displacement of the brachytherapy applicator in relation to the patient during the HDR brachytherapy by processing the images of the at least two markers to determine the displacement of the brachytherapy applicator wherein the processor is further configured to:
      i. perform edge preserved smoothing to images captured by the camera;
      ii. detect edges of the at least two markers;
      iii. reconstruct the at least two markers through morphological analysis;
      iv. determine pixel size to determine a physical distance between the at least two markers; and
      v. measure relative distance change between the at least two markers.

2. The real-time applicator monitoring system of claim 1, wherein the at least one camera comprises at least two cameras.

3. The real-time applicator monitoring system of claim 1, wherein the at least one camera comprises an infrared camera and the at least two markers comprise infrared reflective markers.

4. The real-time applicator monitoring system of claim 3, wherein the at least one camera further comprises an infrared illuminator to illuminate the infrared markers.

5. The real-time applicator monitoring system of claim 3, wherein the infrared reflective markers are self-calibrating.

6. The real-time applicator monitoring system of claim 3, wherein the infrared reflective markers comprise indicators configured to be tracked by the at least one camera.

7. The real-time applicator monitoring system of claim 6, wherein each infrared reflective marker comprises at least two distinguishable indicators so the at least one camera and the computer can determine the orientation of the markers.

8. The real-time applicator monitoring system of claim 1, wherein the at least two markers are configured to be compatible for use during CT and MRI scanning.

9. The real-time applicator monitoring system of claim 1, wherein the at least two markers are configured to minimize displacement and discomfort of the patient.

* * * * *

UNITED STATES PATENT AND TRADEMARK OFFICE
CERTIFICATE OF CORRECTION

PATENT NO. : 10,376,712 B2
APPLICATION NO. : 15/366537
DATED : August 13, 2019
INVENTOR(S) : Xia et al.

Page 1 of 1

It is certified that error appears in the above-identified patent and that said Letters Patent is hereby corrected as shown below:

On the Title Page

The list of inventors should include Wassim Bou-zeid.

Signed and Sealed this
Twelfth Day of November, 2019

Andrei Iancu
*Director of the United States Patent and Trademark Office*